(12) United States Patent
Lapeyre

(10) Patent No.: US 10,182,907 B2
(45) Date of Patent: Jan. 22, 2019

(54) MECHANICAL PROSTHETIC HEART VALVE

(75) Inventor: Didier Lapeyre, Chaignes (FR)

(73) Assignee: NOVOSTIA SA, Neuchatel (CH)

( * ) Notice: Subject to any disclaimer, the term of this patent is extended or adjusted under 35 U.S.C. 154(b) by 632 days.

(21) Appl. No.: 12/598,516

(22) PCT Filed: Apr. 30, 2008

(86) PCT No.: PCT/FR2008/000621
§ 371 (c)(1),
(2), (4) Date: Nov. 2, 2009

(87) PCT Pub. No.: WO2008/152224
PCT Pub. Date: Dec. 18, 2008

(65) Prior Publication Data
US 2010/0131056 A1    May 27, 2010

(30) Foreign Application Priority Data
May 2, 2007  (FR) ..................... 07 03164

(51) Int. Cl.
*A61F 2/24* (2006.01)
(52) U.S. Cl.
CPC ................. *A61F 2/2403* (2013.01)
(58) Field of Classification Search
CPC ........ A61F 2/24; A61F 2/2403; A61F 2/2412; A61F 2/2418; A61F 2/2497; A61F 2002/249
USPC ..... 623/2.23–2.27, 2.12, 2.14, 1.26, 2.1, 2.2
See application file for complete search history.

(56) References Cited

U.S. PATENT DOCUMENTS

| | | | |
|---|---|---|---|
| 4,328,592 A | 5/1982 | Klawitter | |
| 5,123,918 A | 6/1992 | Perrier et al. | |
| 5,314,467 A * | 5/1994 | Shu | 623/2.28 |
| 5,522,886 A | 6/1996 | Milo | |
| 5,545,216 A | 8/1996 | Bokros et al. | |
| 5,628,791 A | 5/1997 | Bokros et al. | |
| 5,641,324 A | 6/1997 | Bokros et al. | |
| 5,772,694 A | 6/1998 | Bokros et al. | |
| 5,814,099 A | 9/1998 | Bicer | |
| 5,843,183 A | 12/1998 | Bokros et al. | |
| 5,861,029 A | 1/1999 | Evdokimov et al. | |
| 5,908,451 A | 6/1999 | Yeo | |

(Continued)

FOREIGN PATENT DOCUMENTS

| | | |
|---|---|---|
| AT | 256441 T | 1/2004 |
| AT | 286372 T | 1/2005 |

(Continued)

OTHER PUBLICATIONS

International Search Report dated Jan. 23, 2009, from corresponding PCT application.

*Primary Examiner* — Christopher D Prone
(74) *Attorney, Agent, or Firm* — Young & Thompson

(57) ABSTRACT

A mechanical prosthetic heart valve, includes an annular support on which at least two movable flaps and several articular extensions are arranged in an articulated manner. Each flap includes a central part framed by two lateral wings that each cooperate with an articular extension by way of an end portion that has an articulation facet. The two articulation facets of each flap together make up a surface area of less than 5% of the total outer surface area of the flap.

34 Claims, 8 Drawing Sheets

(56) References Cited

U.S. PATENT DOCUMENTS

| | | |
|---|---|---|
| 5,908,452 A | 6/1999 | Bokros et al. |
| 5,919,226 A | 7/1999 | Shu et al. |
| 6,051,022 A | 4/2000 | Cai et al. |
| 6,059,826 A | 5/2000 | Bokros et al. |
| 6,096,075 A | 8/2000 | Bokros et al. |
| 6,139,575 A | 10/2000 | Shu et al. |
| 6,176,876 B1 | 1/2001 | Shipkowitz et al. |
| 6,200,340 B1 | 3/2001 | Campbell |
| 6,395,024 B1 * | 5/2002 | Lapeyre et al. ............. 623/2.22 |
| 6,395,025 B1 | 5/2002 | Fordenbacher et al. |
| 6,569,197 B2 | 5/2003 | Samkov et al. |
| 6,582,464 B2 | 6/2003 | Gabbay |
| 6,596,024 B2 | 7/2003 | Chinn |
| 6,610,088 B1 | 8/2003 | Gabbay |
| 6,645,244 B2 | 11/2003 | Shu et al. |
| 6,702,851 B1 | 3/2004 | Chinn et al. |
| 6,723,123 B1 | 4/2004 | Kazatchkov et al. |
| 6,764,509 B2 | 7/2004 | Chinn et al. |
| 6,896,700 B2 | 5/2005 | Lu et al. |
| 6,951,573 B1 | 10/2005 | Dilling |
| 6,991,649 B2 | 1/2006 | Sievers |
| 7,112,220 B2 | 9/2006 | Houston et al. |
| 7,217,287 B2 | 5/2007 | Wilson et al. |
| 7,247,167 B2 | 7/2007 | Gabbay |
| 7,261,732 B2 | 8/2007 | Justino |
| 7,335,218 B2 | 2/2008 | Wilson et al. |
| 7,530,997 B2 | 5/2009 | Roger |
| 7,682,391 B2 | 3/2010 | Johnson |
| 7,776,084 B2 | 8/2010 | Johnson |
| 7,871,435 B2 | 1/2011 | Carpentier et al. |
| 8,052,747 B2 | 11/2011 | Melnikov et al. |
| 8,163,008 B2 | 4/2012 | Wilson et al. |
| 8,506,625 B2 | 8/2013 | Johnson |
| 8,721,716 B2 | 5/2014 | Carpentier et al. |
| 9,155,617 B2 | 10/2015 | Carpentier et al. |
| 9,554,901 B2 | 1/2017 | Cao et al. |
| 9,730,794 B2 | 8/2017 | Carpentier et al. |
| 2001/0025196 A1 | 9/2001 | Chinn et al. |
| 2001/0025197 A1 | 9/2001 | Shu et al. |
| 2001/0049555 A1 | 12/2001 | Gabbay |
| 2002/0022879 A1 | 2/2002 | Samkov et al. |
| 2002/0082689 A1 | 6/2002 | Chinn |
| 2003/0069635 A1 | 4/2003 | Cartledge et al. |
| 2003/0135270 A1 | 7/2003 | Breznock |
| 2004/0092858 A1 | 5/2004 | Wilson et al. |
| 2004/0092989 A1 | 5/2004 | Wilson et al. |
| 2004/0117010 A1 | 6/2004 | Houston et al. |
| 2004/0122515 A1 | 6/2004 | Chu |
| 2004/0127979 A1 | 7/2004 | Wilson et al. |
| 2004/0249451 A1 | 12/2004 | Lu et al. |
| 2005/0021134 A1 | 1/2005 | Opie |
| 2005/0049697 A1 | 3/2005 | Sievers |
| 2005/0075725 A1 * | 4/2005 | Rowe .................. A61F 2/2418 623/2.14 |
| 2005/0137682 A1 | 6/2005 | Justino |
| 2005/0187618 A1 | 8/2005 | Gabbay |
| 2006/0293745 A1 | 12/2006 | Carpentier et al. |
| 2007/0016289 A1 | 1/2007 | Johnson |
| 2007/0016291 A1 | 1/2007 | Johonson |
| 2007/0038295 A1 | 2/2007 | Case et al. |
| 2007/0276479 A1 | 11/2007 | Roger |
| 2008/0147105 A1 | 6/2008 | Wilson et al. |
| 2008/0269879 A1 | 10/2008 | Sathe et al. |
| 2008/0300676 A1 | 12/2008 | Melnikov et al. |
| 2009/0118824 A1 | 5/2009 | Samkov |
| 2011/0015731 A1 | 1/2011 | Carpentier et al. |
| 2011/0054598 A1 | 3/2011 | Johnson |
| 2011/0282440 A1 | 11/2011 | Cao et al. |
| 2012/0123530 A1 | 5/2012 | Carpentier et al. |
| 2012/0203334 A1 | 8/2012 | Wilson et al. |
| 2014/0074228 A1 | 3/2014 | Negri et al. |
| 2014/0222141 A1 | 8/2014 | Carpentier et al. |
| 2015/0012084 A1 | 1/2015 | Wilson et al. |
| 2016/0158013 A1 | 6/2016 | Carpentier et al. |
| 2017/0119523 A1 | 5/2017 | Cao et al. |
| 2017/0333188 A1 | 11/2017 | Carpentier et al. |

FOREIGN PATENT DOCUMENTS

| | | |
|---|---|---|
| AT | 346571 T | 12/2006 |
| AT | 454108 T | 1/2010 |
| AT | 458455 T | 3/2010 |
| AU | 199657328 B2 | 11/1996 |
| AU | 199872844 C | 1/1999 |
| AU | 8497998 A | 2/1999 |
| AU | 1712099 A | 6/1999 |
| AU | 2215399 A | 8/1999 |
| AU | 736769 B2 | 10/1999 |
| AU | 2583200 A | 7/2000 |
| AU | 1068800 A | 6/2001 |
| AU | 2001291074 | 9/2001 |
| AU | 2002231953 | 2/2002 |
| AU | 2003268220 B2 | 3/2004 |
| AU | 2013224679 A1 | 3/2014 |
| BR | 9709968 A | 1/2000 |
| CA | 2 218 621 C | 11/1996 |
| CA | 2 257 205 A1 | 12/1997 |
| CA | 2 263 119 A1 | 2/1999 |
| CA | 2 318 130 A1 | 7/1999 |
| CA | 2 334 433 A1 | 12/1999 |
| CA | 2 253 425 A1 | 5/2000 |
| CA | 2 407 200 A1 | 11/2001 |
| CA | 2 420 049 A1 | 3/2002 |
| CA | 2 503 258 A1 | 3/2004 |
| CA | 2 412 063 A1 | 5/2004 |
| CA | 2 441 846 A1 | 2/2005 |
| CA | 2 610 727 A | 12/2007 |
| CA | 2 714 875 A | 9/2010 |
| CA | 2 793 936 A1 | 9/2012 |
| CA | 2 827 984 A1 | 9/2013 |
| CN | 1223560 A | 7/1999 |
| CN | 1647777 A | 8/2005 |
| CN | 101448470 A | 6/2009 |
| CN | 101217920 B | 3/2011 |
| CN | 102028565 A | 4/2011 |
| CN | 102905648 A | 1/2013 |
| DE | 19624951 A1 | 1/1998 |
| DE | 69630296 T2 | 8/2004 |
| DE | 69630770 T2 | 10/2004 |
| DE | 103 40 265 A1 | 4/2005 |
| DE | 69829070 T2 | 7/2005 |
| DE | 69634146 T2 | 12/2005 |
| DE | 69732190 T2 | 12/2005 |
| DE | 69930500 T2 | 11/2006 |
| DE | 69834254 T2 | 2/2007 |
| DE | 69933052 T2 | 3/2007 |
| DE | 60124930 T2 | 9/2007 |
| EP | 0 383 676 A1 | 8/1990 |
| EP | 0 790 043 B1 | 8/1997 |
| EP | 0 825 841 B1 | 3/1998 |
| EP | 0 998 244 B1 | 5/2000 |
| EP | 1 011 539 B1 | 6/2000 |
| EP | 1 018 989 A1 | 7/2000 |
| EP | 1 035 811 B1 | 9/2000 |
| EP | 1 049 426 B1 | 11/2000 |
| EP | 1 155 666 A1 | 11/2001 |
| EP | 1 294 316 A1 | 3/2003 |
| EP | 1 318 775 B1 | 6/2003 |
| EP | 1 338 255 B1 | 8/2003 |
| EP | 1 357 862 A1 | 11/2003 |
| EP | 0 910 312 B1 | 12/2003 |
| EP | 1 729 687 | 1/2004 |
| EP | 1 592 367 B1 | 11/2005 |
| EP | 1 703 865 B1 | 9/2006 |
| EP | 1 734 902 B1 | 12/2006 |
| EP | 1 901 682 B1 | 3/2008 |
| EP | 1 906 873 A2 | 4/2008 |
| EP | 1 946 724 A1 | 7/2008 |
| EP | 1 977 718 B1 | 10/2008 |
| EP | 2 010 101 A1 | 1/2009 |
| EP | 2 568 925 B1 | 3/2013 |
| EP | 3 009 105 B1 | 4/2016 |

(56) References Cited

FOREIGN PATENT DOCUMENTS

| | | |
|---|---|---|
| ES | 2 203 699 T3 | 4/2004 |
| ES | 2 213 827 T3 | 9/2004 |
| ES | 2 234 171 T3 | 6/2005 |
| ES | 2 276 823 T3 | 7/2007 |
| GB | 2 371 988 B | 8/2002 |
| JP | H04267192 A | 9/1992 |
| JP | 2000513250 A | 10/2000 |
| JP | 2000517207 A | 12/2000 |
| JP | 2001525223 A | 12/2001 |
| JP | 2002500923 A | 1/2002 |
| JP | 2002516710 A | 6/2002 |
| JP | 2002537001 A | 11/2002 |
| JP | 2003531678 A | 10/2003 |
| JP | 2004510471 A | 4/2004 |
| JP | 3 594 973 B2 | 9/2004 |
| JP | 2007503856 A | 3/2007 |
| JP | 2007518496 A | 7/2007 |
| JP | 4 074 430 B2 | 2/2008 |
| JP | 4 080 690 B2 | 2/2008 |
| JP | 2009501058 A | 1/2009 |
| JP | 4 494 421 B2 | 4/2010 |
| JP | 4 545 149 B2 | 7/2010 |
| JP | 2013039428 A | 2/2013 |
| JP | 5 285 425 B2 | 6/2013 |
| MX | PA02010798 A | 7/2003 |
| RU | 2113191 C1 | 6/1998 |
| RU | 2146906 C1 | 3/2000 |
| RU | 2157674 C1 | 10/2000 |
| RU | 2 302 220 C1 | 7/2007 |
| RU | 2006110832 A | 10/2007 |
| RU | 2325874 C2 | 6/2008 |
| TW | 590007 U | 6/2004 |
| WO | 92/16169 | 10/1992 |
| WO | 96/36299 A2 | 11/1996 |
| WO | 97/49357 A1 | 12/1997 |
| WO | 98/06358 A1 | 2/1998 |
| WO | 98/51239 A1 | 11/1998 |
| WO | 99/04731 A1 | 2/1999 |
| WO | 99/26560 A1 | 6/1999 |
| WO | 99/29270 A1 | 6/1999 |
| WO | 99/37249 A1 | 7/1999 |
| WO | 99/62437 A1 | 12/1999 |
| WO | 00/38595 A1 | 6/2000 |
| WO | 00/38597 A1 | 7/2000 |
| WO | 01/34068 A1 | 5/2001 |
| WO | 01/82840 A1 | 11/2001 |
| WO | 02/24119 A1 | 3/2002 |
| WO | 02/49689 A2 | 6/2002 |
| WO | 02/054987 A2 | 7/2002 |
| WO | 02/062271 A1 | 8/2002 |
| WO | 2004/019811 A2 | 3/2004 |
| WO | 2005/004754 A3 | 1/2005 |
| WO | 2005023155 A1 | 3/2005 |
| WO | 2005/051226 A2 | 6/2005 |
| WO | 2005/070342 A1 | 8/2005 |
| WO | 2005/072654 A1 | 8/2005 |
| WO | 2007/016097 A2 | 2/2007 |
| WO | 2007/075121 A1 | 7/2007 |
| WO | 2007/113609 A1 | 10/2007 |
| WO | 2011/143473 A2 | 11/2011 |
| ZA | 200808779 B | 11/2009 |

\* cited by examiner

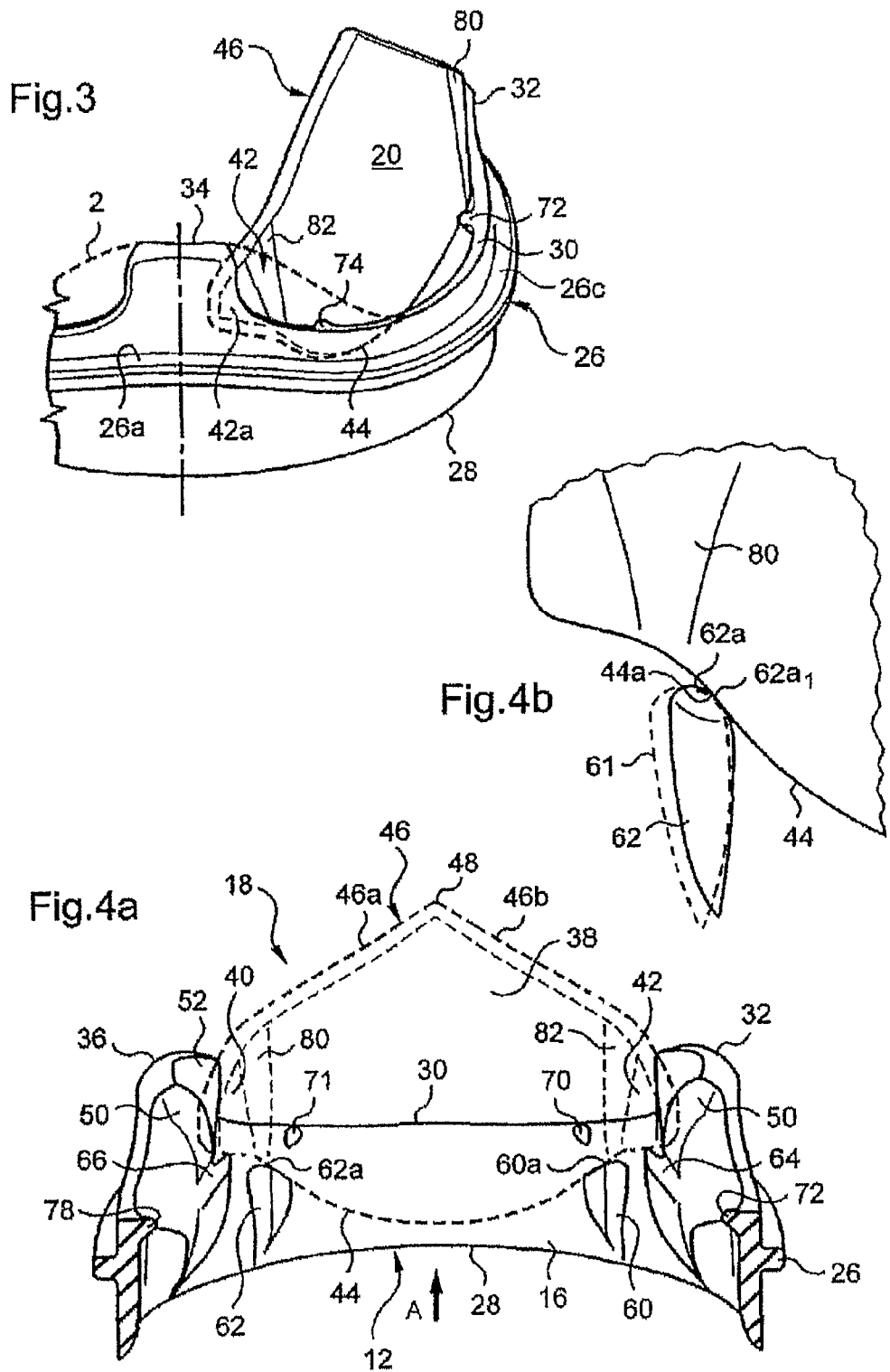

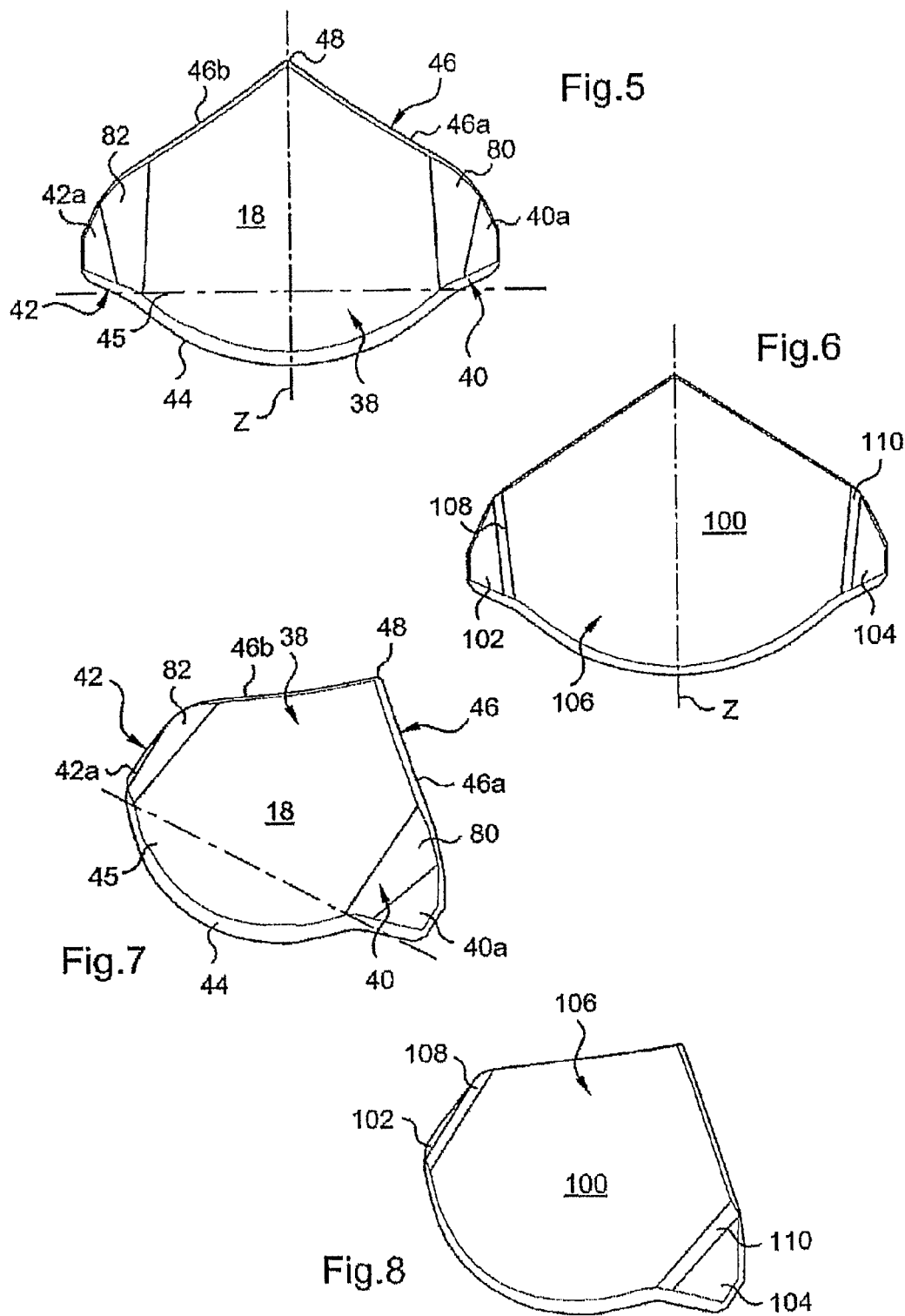

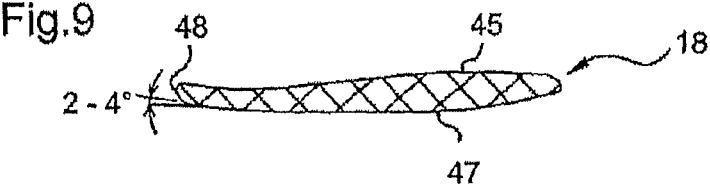
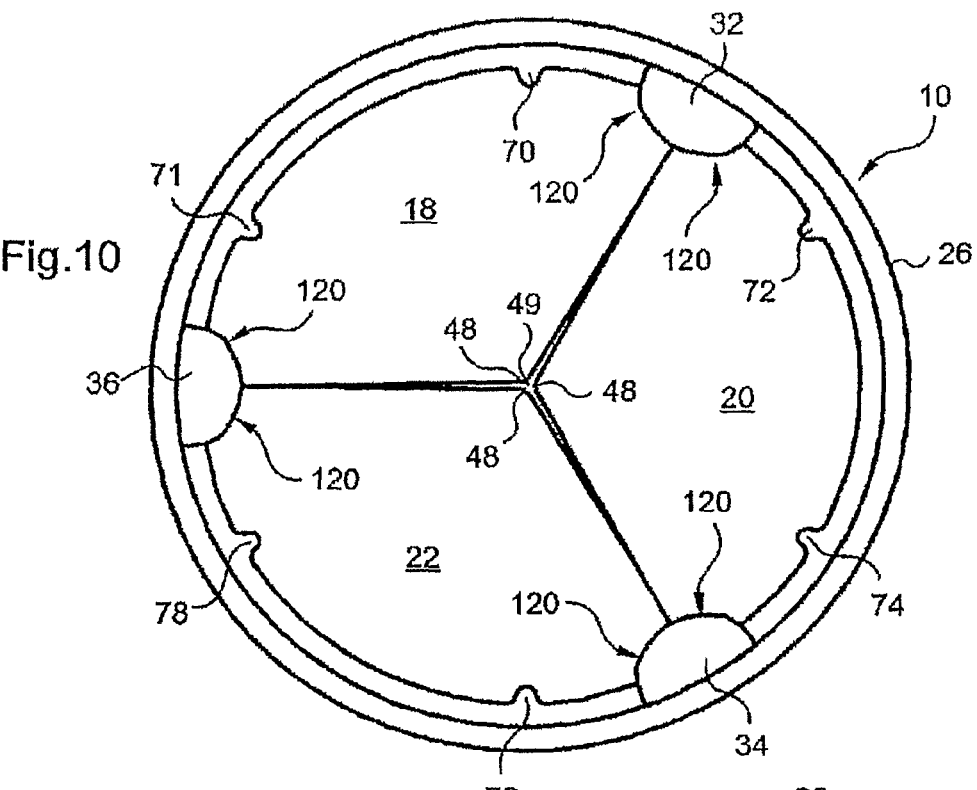
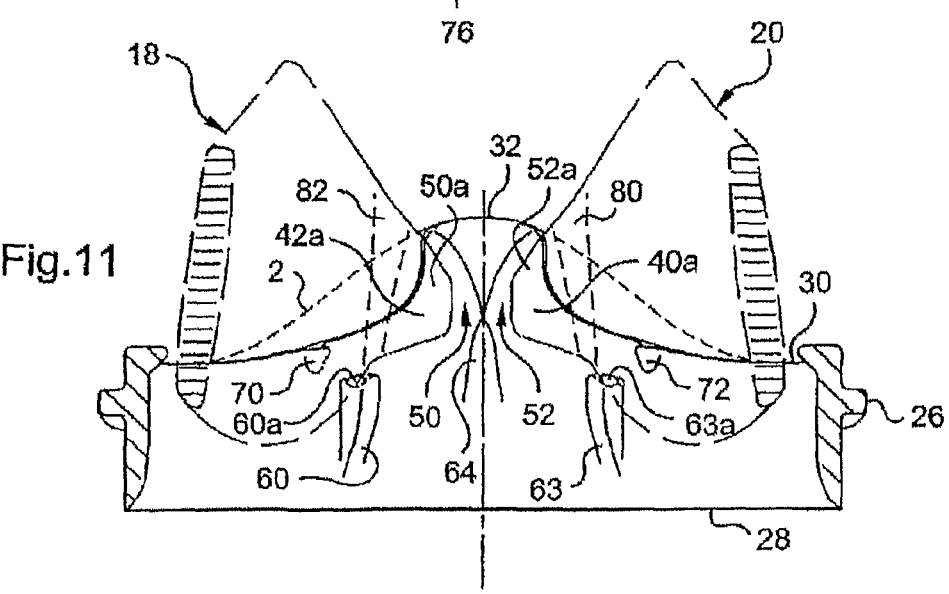

MECHANICAL PROSTHETIC HEART VALVE

The present invention concerns a mechanical prosthetic heart valve.

BACKGROUND OF THE INVENTION

At present, approximately 300 000 patients worldwide benefit each year from a valve prosthesis replacing one or more of their heart valves damaged either by infectious disease or by a degenerative process linked to aging.

There are two major families of prosthetic heart valves:
valve prostheses of biological origin, known as bioprostheses, which are either removed from the animal and treated chemically or constructed from biological tissues on the model of a natural valve;
mechanical valve prostheses, which are devices unrelated to the shape of a natural valve and manufactured from biologically compatible man-made materials resistant to wear.

Because of their anatomical configuration and their physiological mode of operation, bioprostheses offer biological performance comparable with that of a natural heart valve because they respect the natural structure of the flow of blood through the cavities of the heart and the aorta.

This feature of bioprostheses saves patients lifelong anticoagulant treatment, which eliminates the risk of hemorrhage following long-term use of these drugs and therefore improves the quality of life of these patients.

Thus patients may even forget that they have an artificial heart valve.

Moreover, it is necessary to note that bioprostheses do not cause any acoustic disturbance, which also helps patients to forget that they have an artificial heart valve.

These bioprostheses have a limited service life, however, because of unavoidable calcification over time, which imposes their replacement after a period of about ten years on average. Once started, this calcification accelerates and destroys the valve, with the consequence of progressive deterioration of the valve function and its repercussions on the heart muscle. This calcification occurs more quickly in young persons than in elderly persons, which limits the field of application of bioprostheses to persons aged 65 or more or persons whose life expectancy is less than the service life of the bioprosthesis.

In France the life expectancy at age 65 is 17.7 years for men and 21.7 years for women and replacing a defective heart valve is regarded as major surgery that is accompanied, beyond the age of 75, by a high mortality rate. To this risk is added the discomfort, at this age, of major surgery.

In contrast to bioprostheses, mechanical artificial valve devices are not degradable and have a service life exceeding the human lifetime. On the other hand, because their geometry departs very considerably from the natural model and because of their non-physiological mode of operation, these mechanical valves generate on each heart beat disturbances to the flow of blood in the form of turbulence, areas of recirculation, vortices, shearing of the blood cells and slowing or stasis of the flow over the parts of the mechanical device that are poorly swept by the blood flow, notably the articular areas.

These disturbances to the flow increase the time of contact of the blood cells with and the intensity of the reactions of active proteins on the prosthetic materials constituting these devices. Any foreign material in contact with the blood inherently stimulates the coagulation process. There results from interaction between the disturbances to the flow and the non-biological materials:
adhesion to the surface of these materials of active proteins and blood platelets,
activation of coagulation, and
formation on the surfaces of organized bloodclots.

This powerful biological phenomenon is the same as that which governs the physiological process of healing the internal wall of the blood vessels. It prevents blood leaking out of the circulatory system. It is therefore indispensable to life and difficult to counteract.

However, not only can coagulation deposits impede the mechanical function of the valve on blood circulation, which puts the life of the patient at risk, but these deposits can also migrate in the circulatory system (embolisms), most often in the cerebral circulatory system, and lead to neurological problems, often with invaliding repercussions.

To these coagulation phenomena is added trauma of the red cells, repeated on each cardiac cycle, which shortens their life (hemolysis) and leads to chronic inflammatory reaction of the entire organism. This reaction itself tends to increase the coagulability of the blood, which increases the probability of coagulation incidents.

Thus thrombosis generates thrombosis and creates a self-sustaining chronic illness.

To remedy this drawback, any patient with a mechanical artificial valve device must be protected for their entire life by anticoagulation treatment, with the inherent risk either of hemorrhage in the event of an overdose or of thrombosis/embolism incidents in the event of underdosing.

Since the beginning of the sixties, a number of generations of mechanical heart valves have been designed to reduce the disturbance to the blood flow that these devices generate, so as to reduce the risk of coagulation: firstly, valve prostheses consisting of a ball floating in a cage (STARR-EDWARD), then, at the beginning of the seventies, second generation prostheses consisting of a pivoting disk (BJÖRK-SHILEY) and then, ten years later, third generation prostheses with two flaps and lateral openings (ST-JUDE MEDICAL). This third generation is that most widely used at present and produced in different forms by a number of manufacturers.

Despite these improvements, third generation valves still cause blood trauma and still cannot function in man without anticoagulant drugs. On the other hand, thanks to more than 40 years of clinical experience, the anticoagulation treatment is now well codified.

Patients with a mechanical valve in the aortic position must maintain their blood coagulability (as measured by a standardized biological method known as the international normalized ratio (INR) method) at a level at least two and a half times greater than the physiological value (INR 2.5).

Patients with a mechanical valve in the mitral position must maintain their blood coagulability at a level at least three and a half times the physiological value (INR 3.5).

This difference of in the "harmfulness" of mechanical prostheses between the aortic position and the mitral position is a result of the fact that blood flows more slowly through the mitral orifice than through the aortic orifice. The time to fill the heart through the mitral valve (typically of the order of 450 milliseconds at 70 beats per minute) is longer than the time to eject the blood through the aorta (typically of the order of 300 milliseconds). The blood is therefore in contact with a prosthetic valve in the mitral position for longer, which enables coagulation processes to complete.

Moreover, mitral valves are larger, and so the areas of foreign materials exposed to biological deposits are greater. Thus it has been established that the risk of thrombosis/embolism complications in patients with mechanical heart valves is twice as high for the mitral position as for the aortic position.

For large numbers of patients with mechanical heart valves, the average rate of coagulation incidents under current medical practice is statistically less than 3% per annum and per patient and the rate of hemorrhage is less than 4% per annum per patient.

This state of the art data provides a benchmark for clinicians to evaluate the thrombogenetic potential of a new mechanical heart valve during probationary testing in man and is decisive for obtaining authorization to place it on the market. A rate of thrombosis/embolism or hemorrhage complications greater than 3-4% will lead to rejection of the product by the medical community and refusal of licenses.

As long as the anticoagulant protection is correctly administered, millions of patients with mechanical heart valves worldwide can nevertheless now live under acceptable conditions. These patients, who were previously condemned to die within a short time, now live on for many years. However, their life expectancy, given the risk of thrombosis/embolism and hemorrhage, remains significantly less than that of persons of the same age without a heart valve.

The imperative requirement for anticoagulation protection for all patients with mechanical heart valves is particularly dramatic in countries where the medical infrastructure does not provide satisfactory monitoring of anticoagulation treatment. In those countries, valve disease is becoming endemic and is more likely to affect younger persons, women and the mitral valves. For example, in India several million children under the age of 15 need a prosthetic valve replacement. These young persons are poor candidates for biological type valves because of the calcification problems referred to above. Mechanical heart valves are therefore more willingly employed but are accompanied by a rate of dysfunction through coagulation that is very much higher than is observed in developed countries, and this major risk is restricting their use. In these countries the thrombogenetic nature of mechanical heart valves represents a public health problem and illustrates the need for better performing products whose use would impose fewer constraints.

It should be noted that even if the anticoagulation treatment is followed correctly, the rate of complication remains of concern even in countries in which the medical infrastructures are adequate. Statistically speaking, over a period of 10 years, one in two mechanical heart valve patients will have experienced a serious complication necessitating hospitalization, either because of a coagulation incident or because of a hemorrhage.

Mechanical heart valve designers are therefore seeking to improve the hydrodynamic performance and the mode of operation of these devices to reduce the disturbances that they cause in the flow of blood and thereby to eliminate or at least to reduce the doses of anticoagulation drugs necessary to prevent these complications.

There is known from U.S. Pat. No. 6,395,024 a mechanical prosthetic heart valve that includes a ring with an interior peripheral surface centered on an axis and three flaps disposed in the vicinity of the interior peripheral surface of the ring. These three flaps are adapted to pivot between a closed position preventing blood from flowing through the valve and an open position in which blood flows axially through the valve.

The ring has an edge called the downstream edge that connects the interior peripheral surface to an exterior peripheral surface and is on the downstream side of the flow and three crenelations or protuberances that extend axially in the downstream direction from this edge.

Each flap has a central part provided with two lateral wings each of which cooperates with respective means for guiding rotation of the valve provided on the interior surfaces of two consecutive crenelations. The space in which each lateral wing of a flap pivots is called the pivoting space.

Also, two windows are formed symmetrically in each crenelation.

Each window enables satisfactory rinsing of the external face of the lateral wings of the flaps by the retrograde flow.

Accordingly, when the valve is installed in the mitral position, this external face can be swept by the flow of blood circulating from the ventricle toward the aorta. Thus, thanks to this feature, all risk of biological deposits at this location is eliminated.

Likewise, when the valve is installed in the aortic position, the reflux of blood through these windows into the aortic sinuses when the valve is closed can rinse the external face of the lateral wings, preventing a volume of blood from being trapped in the pivoting spaces of the flap.

To perfect this protection against stagnation of blood in the pivoting spaces, an additional feature has been provided: the lower edge of the windows described above forms with the leading edge of the lateral wings of the flaps, when the latter are open, a second opening having a triangular sluice shape. This second opening (called a "cleft") is "dynamic" in the sense that the area of the orifice formed in this way increases progressively as the flap moves from the closed position to the open position. It allows direct passage to the exterior of the flaps of blood conveyed by the anterograde flow and assures additional sweeping of the leading edge and the external face of the wings of the flaps.

The Applicant has nevertheless noticed from implantation in animals that the effect of this additional feature on the flow of blood is not the same in the mitral position as in the aortic position.

The above feature proved to be efficacious on a large number of animals implanted with the valve in the mitral position and left for many months without anticoagulation protection, whereas this was not the case with animals in which the same valve had been implanted in the aortic position.

In the mitral position, during ventricular filling, low-pressure blood can flow through the second openings ("clefts") from the interior of the valve toward the exterior in the pivoting spaces of the flaps and rinse these critical pivoting spaces.

However, during ventricular ejection, the blood pressure generated by the heart on a valve implanted in the aortic position is ten times greater than the blood pressure that is exerted via a valve implanted in the mitral position.

Because aortic valves are smaller than mitral valves and the clefts are therefore much narrower, in the aortic position the effect of rinsing is to create, on each heart beat, powerful lateral "jets" that go beyond the intended objective of rinsing to the point of causing trauma to the blood cells.

The trauma threshold recognized in the prior art in this connection is situated at a force of around 150 dynes/cm$^2$ for blood platelets and 1000 dynes/cm$^2$ for red cells. Beyond these values, blood components are sheared and the blood platelets release their coagulating agents, which can cause coagulation complications.

Thus clefts that are efficacious in the mitral position to prevent slowing of the blood in the pivoting spaces are of no utility and potentially dangerous in the aortic position.

Clinical experience has shown that the articulation areas of a mechanical heart valve are the areas most exposed to coagulation phenomena.

Unfortunately, as a heart valve assures on each heart beat a function that is vital to the circulation of the blood, the specifications imposed by functional safety imperatives have to take priority over coagulation problems.

Thus the flap articulation mechanism imposes a geometry that is not favorable to a good blood flow structure in the pivoting spaces. It generates shear and microturbulence in the immediate vicinity of surfaces that are relatively poorly swept by the blood stream.

The amplitude of this phenomenon is linked to the number of articulation areas of the valve. It is therefore greater for a heart valve with three flaps that comprises six pivoting spaces than for a heart valve with two flaps, which has only four such spaces.

Because of this, the advantages of the mechanical heart valve with three flaps where resistance to coagulation complications is concerned are found to be greatly reduced if specific devices are not fitted.

Patients who need a prosthetic heart valve wish to be operated on only once and to be protected from coagulation complications that can arise if foreign bodies are present in the circulatory system.

Unfortunately, to prevent coagulation deposits forming, patients are obliged to take anticoagulant drugs throughout their life, which is a constraint, and long-term use of such drugs is liable to induce hemorrhage complications.

SUMMARY OF THE INVENTION

The present invention aims to remedy at least one of the drawbacks of the prior art by proposing a mechanical prosthetic heart valve, characterized in that it comprises:
- an annular support having an internal peripheral surface centered on a longitudinal axis X, and
- at least two mobile flaps articulated to the internal peripheral surface of the support so that each is able to rotate about a flap rotation axis perpendicular to the longitudinal axis from an open position of the valve in which the open flaps delimit between them a main orifice centered on the longitudinal axis and through which the blood flows axially to a closed position of the valve in which the closed flaps prevent the blood from flowing back through the main orifice, the annular support having an edge on the downstream side of the anterograde flow, called the downstream edge, and a plurality of articular extensions that extend axially from the downstream edge and the number of which corresponds to the number of flaps, each flap having a central part symmetrically bracketed by two lateral wings that are inclined relative to this central part, these two wings respectively cooperating, to allow rotation of the flap, with the internal surfaces of two articular extensions via a so-called terminal portion of each wing, each terminal portion having an exterior surface, called the articulation facet, which when the flap is open comes to bear against a portion of the internal surface of the corresponding articular extension, called the extension facet, the two articulation facets of each flap together adding up to an area substantially less than 5% of the total exterior area of the flap.

By drastically reducing the exterior area of each lateral wing of the flaps in contact, in the open position, with the corresponding articular extension of the support, the exterior area of the flaps that is not in direct contact with the flow of blood in this position is considerably reduced.

In this way, whether the valve is implanted in the mitral position or the aortic position, the exterior surface of the flaps is swept better by the flow of blood than before, especially in the area of the lateral wings of the flaps.

The considerable reduction of the bearing area of the flaps in the open position eliminates the necessity to provide rinsing openings in the area of the articular extension as described in the aforementioned prior art document U.S. Pat. No. 6,395,024.

The notches formed on each side of the articular extensions, even at their apex, remove a significant quantity of material that is reactive vis à vis the blood flow, which improves the resistance of the valve of the invention to coagulation deposits and more generally its fluidic performance.

Reducing the bearing area of the flaps does not compromise the operation of the valve because, as the Applicant has noted, it is not necessary for the flap to bear on the valve support when open, in contrast to what occurs on closure, when the hydrodynamic forces exerted on the bearing abutments are much higher.

In fact, in the open position the force exerted by the flow on the flap and therefore on the portion of the internal surface of the articular extensions is minimal.

What is more, the invention considerably reduces the risk of the valves jamming in the open position, which could occur through penetration of a coagulation deposit between the exterior surfaces of the lateral parts of the flaps and the facing interior surfaces of the corresponding articular extensions.

If this were to occur, the angle of opening of the flap or flaps concerned would be reduced, the consequence of which would be to create a disturbance of the flow liable to lead to aggravation of the phenomenon and finally to immobilization of the flap or flaps in the closed position.

Apart from the possibility of articular thrombosis impeding the operation of the flap, this interposition of coagulation deposits can also cause embolisms in the peripheral blood flow.

Thus the invention eliminates or at least drastically reduces the need to take anticoagulant drugs.

On the flaps of a heart valve from the aforementioned prior art (see FIGS. 6 and 8), the junction area between each lateral wing and the central part of the flap has a small radius of curvature that imparts to this area the general shape of an edge.

Through analysis of the microstructure of the flow of blood at this location when the flaps are in the open position, the Applicant has noticed the presence downstream of the junction area, in the vicinity of the pivoting spaces, of a turbulent microstream that is reproduced on each cycle.

Now, blood turbulence and the increase in the time that red cells and platelets are present at this location encourages the formation and attachment of bloodclots to the adjoining immobile surfaces.

To eliminate this local disturbance of the flow each lateral wing of each of the flaps is connected to the central part of the flap by a junction area the exterior surface whereof is convex and which, over at least part of its length including the part of the area situated on the downstream side of the anterograde flow (trailing edge), has a radius of curvature sufficiently large to prevent the formation of turbulent flow in the vicinity of this junction surface.

This feature reduces localized distortion of the flow in the vicinity of the pivoting spaces of the flaps, the flow then following the exterior surface of the flaps without separating from them.

What is more, the consequence of increasing the radius of curvature is to keep the part of the flap to which this modification of the radius of curvature relates in a flow area subjected to a speed gradient close to that to which the rest of the flap is subjected, further attenuating distortion of the flow in this critical area. The part of the flap to which this particular feature relates is that starting at a distance of approximately 20% from the leading edge of the flap, for example.

This radius of curvature depends on the dimensions of the flap and can be determined by the person skilled in the art to obtain the required effect for each size of valve.

With the aforementioned configuration, the angle formed between each lateral wing and the central part of the external face of the flap is increased relative to that of the prior art flaps.

According to one feature the radius of curvature of the part of the junction area situated on the downstream side of the flow is at least 2 mm for a valve intended to be implanted in the aortic position and at least 3 mm for a valve intended to be implanted in the mitral position.

According to another feature each lateral wing of each of the flaps is connected to the central part of the flap by a junction area the exterior surface whereof is convex and has the general shape of a portion of a cone the apex of which is on the upstream side of the anterograde flow.

According to this feature, the radius of curvature between each lateral wing and the central part of the flap is not significantly modified in the immediate vicinity of the leading edge of the flap but is progressively modified on approaching the trailing edge of the flap (the edge of the flap situated on the downstream side of the flow).

Thus this modification of the radius of curvature of the flap in the junction area does not modify the contour of the leading edge of the flap, and therefore does not modify that of the points at which it bears on the interior surface of the annular support during rotation of the flap from its open position to its closed position.

According to one feature each lateral wing of each of the flaps is joined to the central part of the flap by a junction area the exterior surface of which is convex and has a part-cylindrical general shape.

According to one feature the rotation axis of each flap is a virtual axis situated externally of the flap, between the latter and the annular support, and extends in a direction from one lateral wing of the flap to the opposite lateral wing.

According to one feature, in a plane perpendicular to the longitudinal axis X of the valve, the flap rotation axis is at a distance from the longitudinal axis X that is greater than 75% of the radius of the annular support.

According to one feature each of the articulation facets of a flap and the corresponding extension facet of the articular extension concerned define between them, when the flap is in its closed position, a flap pivoting space that disappears when the articulation facet of the flap comes, in its open position, to bear against the corresponding extension facet.

According to one feature the volume of the pivoting space is less than $2/100^{th}$ of the volume displaced by the flap when it moves from the closed position to the open position.

According to one feature the exterior surface of the central part of the flap has a substantially convex general shape in a direction from one lateral wing of the flap to the opposite lateral wing.

According to one feature the central part of each flap has an interior surface facing toward the main orifice of the valve that has a substantially concave general shape in a direction from one lateral wing of the flap to the opposite lateral wing.

According to one feature, when the valve is in its open position, the main orifice delimited by the interior surfaces of the flaps has, projected in a plane perpendicular to the longitudinal axis of the annular support, a flow section offered to the flow that is equal at least to 75% of the internal area delimited in the same plane by the annular support.

According to one feature, when the valve is in its open position, each flap defines a secondary orifice between its exterior surface and the internal peripheral surface portion of the annular support that separates the two articular extensions with which the flap cooperates.

According to one feature each secondary orifice has a crescent moon general shape.

According to one feature the dimension of the secondary orifice in a radial direction projected in a plane perpendicular to the longitudinal axis of the annular support is less than 20% of the inside radius of the annular support.

According to one feature each secondary orifice has in a plane perpendicular to the longitudinal axis of the annular support a flow section offered to the flow that is less than 7% of the internal area delimited in the same plane by the annular support.

According to one feature none of the articular extensions has an opening through it.

According to one feature for each flap the annular support has on its internal peripheral surface in the vicinity of the downstream edge two stops causing the flap to pivot immediately into its open position when the pressure of the flow of blood is exerted on the internal face of this flap.

According to one feature for each flap the annular support has on its internal peripheral surface two supporting means for supporting the flap in its closed position, said supporting means for each flap being between the two articular extensions with which the respective lateral wings of the flap cooperate.

According to one feature, projected in a plane perpendicular to the longitudinal axis of the annular support, each stop is spaced angularly from the nearest supporting means by a distance substantially corresponding to at least half the width of said supporting means, the width being measured in the plane concerned in a tangential direction relative to the annular support.

According to one feature the stops for each flap are between the supporting means of the flap.

According to one feature each flap has at its periphery a leading edge that is on the upstream side of the anterograde flow of blood and cooperates with the internal surface of the annular support in the closed position of the flap and a trailing edge on the downstream side of the anterograde flow.

According to one feature each of the flap supporting means cooperates with a contact area of the leading edge of the flap through surface contact not line contact on closure of said valve.

According to one feature each flap supporting means has an upper end surface a portion whereof on the side opposite the nearest articular extension has a radius of curvature sufficiently large to cooperate with surface contact not line contact with the transverse rectilinear contact area of the leading edge of the flap.

According to one feature the trailing edge of each flap has a substantially triangular shape and in the closed position of the valve the trailing edges of the three flaps cooperate with each other to form a trihedron the apex of which is directed downstream.

According to one feature each flap has, in its central part, at the trailing edge, an area aligned with the axis of symmetry of the flap that is substantially ski tip shaped at its downstream free end, the substantially ski tip shaped end of the flap forming a point that diverges from the extension of the interior surface of said flap at an angle substantially between 2° and 4° inclusive.

According to one feature in the closed position of the valve the three substantially ski tip shaped ends of the flaps remain at a distance from each other of at least 50 microns and produce between them a central interstice in the shape of a star with three points.

According to one feature each of the three points extends over a distance corresponding at least to one third of the total length of the trailing edge of the flaps.

According to one feature each flap in its closed position forms with a plane perpendicular to the longitudinal axis (X) of the annular support a closure angle between 30° and 50° inclusive and in its open position is substantially parallel to the direction of the flow.

According to one feature the closure angle is between 40° and 50° inclusive for valves intended to be implanted in the mitral position.

According to one feature each flap has on its exterior surface one or more areas provided with grooves that encourage orientation of the blood flow toward the lateral wings of the flap.

According to one feature, in valves intended to be implanted in the aortic position, the annular support has on its exterior peripheral surface a peripheral rib for fixing a ring of suture, the rib being configured so that its general shape reproduces the profile of a substantially sinusoidal curve having an apex in line with each articular extension and a hollow between two consecutive articular extensions.

Another aspect of the invention provides a mobile flap intended to be mounted on an annular support of a mechanical prosthetic heart valve, having at its periphery a leading edge that is intended to be disposed on the upstream side of the anterograde blood flow and a trailing edge that is intended to be disposed on the downstream side of that flow, the flap having a central part symmetrically bracketed by two lateral wings that are inclined relative to the central part, each lateral wing being joined to the central part by a junction area the exterior surface whereof is convex and which, over at least part of its length including the trailing edge, has a radius of curvature sufficiently large to prevent the formation of turbulent flow in the vicinity of that junction surface.

According to one feature the radius of curvature of the junction area in line with the trailing edge is at least 2 mm for a valve intended to be implanted in the aortic position and at least 3 mm for a valve intended to be implanted in the mitral position.

According to one feature the exterior surface of the junction area has the general shape of a portion of a cone the apex of which is situated on the side opposite the trailing edge of the flap.

According to one feature the exterior surface of the junction area has a part-cylindrical general shape.

According to one feature the flap includes an exterior surface and an interior surface opposite each other and each connecting the leading edge to the trailing edge.

According to one feature the exterior surface of the central part of the flap has a general shape that is substantially convex in a direction from one lateral wing of the flap to the opposite lateral wing.

According to one feature the interior surface of the central part of the flap has a general shape that is substantially concave in a direction from one lateral wing of the flap to the opposite lateral wing.

According to one feature the flap has on its exterior surface one or more areas provided with grooves that encourage orientation of the blood flow toward the lateral wings.

According to one feature the flap has in its central part, at the trailing edge, an area aligned with the axis of symmetry of the flap that is substantially ski tip shaped at its free end, the substantially ski tip shaped end of the flap forming a tip that diverges from the extension of the interior surface of said flap at an angle substantially between 2° and 4° inclusive.

According to one feature the flap is rigid.

According to one feature the flap is produced from a biocompatible material and at will in monolithic carbon, in graphite with a pyrolytic carbon coating or in a synthetic polymer having wear resistance properties comparable to those of pyrolytic carbon.

BRIEF DESCRIPTION OF THE DRAWINGS

Other features and advantages will become apparent in the course of the following description, which is given by way of nonlimiting example only and with reference to the appended drawings, in which:

FIG. 3 is a diagrammatic partial view showing the cooperation of a flap in its open position with an articular extension of the invention and a prior art articular extension (in dashed outline), as seen from the exterior of the valve;

FIG. 4a is a diagrammatic partial view in perspective of the interior of the valve, showing the arrangement of a flap in its open position accommodated between two articular extensions of the support;

FIG. 4b is a diagrammatic partial view to a larger scale of support means cooperating with the leading edge of a flap;

FIGS. 5 and 7 are respectively diagrammatic front and perspective views of the exterior surface of a flap of the invention;

FIGS. 6 and 8 are respectively diagrammatic front and perspective views of the exterior surface of a flap of the prior art;

FIG. 9 is a view of a flap of the invention in cross section in a plane containing the axis Z of symmetry;

FIG. 10 is a diagrammatic top view of a valve of the invention with the flaps in their closed position;

FIG. 11 is a diagrammatic partial view showing the arrangement of the lateral wings of two flaps in their open position relative to an articular extension 32 of the valve;

DETAILED DESCRIPTION OF THE PREFERRED EMBODIMENTS

As represented in FIGS. 1 to 4b a mechanical prosthetic heart valve 10 of the invention includes an annular support 12 in the form of a ring that defines inside the latter an internal passage 14 for the cyclic flow of blood caused by cardiac contractions.

Figures 1, 2:
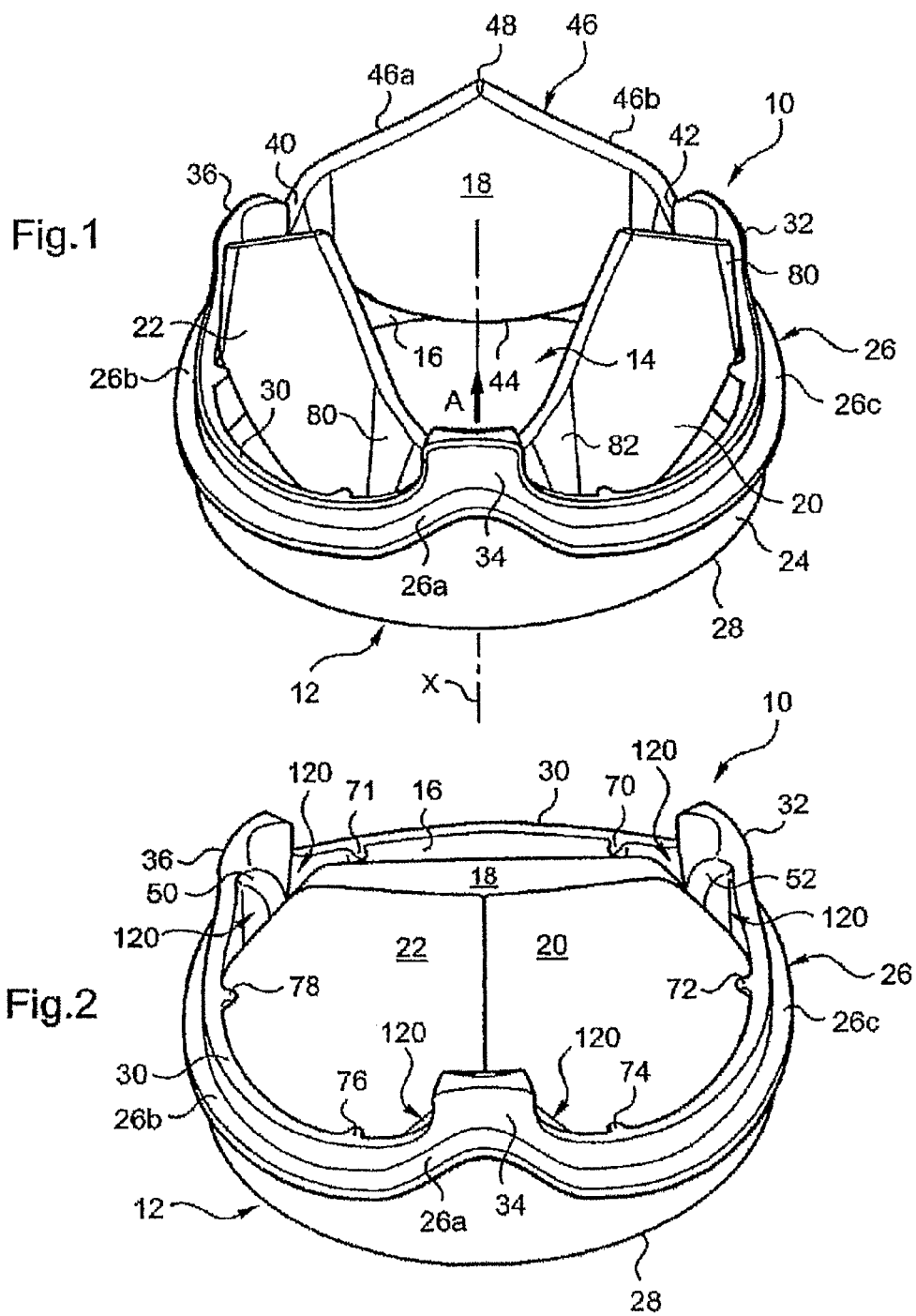
FIG. 1 is a diagrammatic perspective view of a valve of the invention with the flaps in their open position.
FIG. 2 is a diagrammatic perspective view of the FIG. 1 valve with the flaps in their closed position.

The flow through the valve 10 in its open position is referred to as the anterograde flow and its direction of flow is indicated by the arrow A in FIG. 1.

Conversely, the stream flowing in the reverse direction during closure of the valve is referred to as the retrograde flow.

The central internal passage 14 for the flow of blood is delimited by the interior peripheral surface 16 of the annular support 12, which supports three mobile flaps 18, 20, 22 described in detail hereinafter.

As shown in FIGS. 1 and 2, the heart valve 10 is centered on a longitudinal axis X and has symmetry of revolution about that axis.

The annular support 12 also has an exterior peripheral surface 24 with a peripheral rib 26 intended to receive a ring of suture, not shown, of textile, for example, enabling the surgeon to fix the valve to the heart tissue by suture points in known manner.

In FIG. 1 the valve is shown in its open position in which the flaps 18, 20 and 22 are in a raised or open position, the flow of blood passing through the valve in the anterograde direction, while in FIG. 2 the valve is represented in its closed position with the flaps in a lowered or closed position.

It will be noted that, without this impacting on the principle of the invention, the valve can include more than three flaps or only two flaps, in which case the annular support 12 is elliptical and the flaps are oval.

In this regard, a valve designed to be implanted in the mitral position has two oval flaps, for example, but could equally have three flaps of some other shape.

The annular support 12 has on the upstream side of the anterograde flow an upstream edge or leading edge 28 connecting the interior peripheral surface 16 to the exterior peripheral surface 24.

The annular support also has on the downstream side of the anterograde flow a downstream edge or trailing edge 30 also connecting the interior peripheral surface 16 to the exterior peripheral surface 24 of the annular support.

The support 12 also includes three articular extensions or protruberances 32, 34, 36 which extend downstream from the downstream edge 30, parallel to the direction of the longitudinal axis X, and which thus form crenelations extending axially relative to the peripheral edge 30 and the base of which is of substantially the same width (the dimension perpendicular to the axis X) as the apex.

These extensions accommodate the articulation areas with which the mobile flaps cooperate to pass from their open position to their closed position and vice versa.

It will furthermore be noted that the width of the articular extensions at their apex is substantially equal to the width of the articular areas.

These articular extensions 32, 34, 36, equal in number to the flaps, have smaller dimensions than the crenelations equipping prior art heart valves, as represented diagrammatically in the FIG. 3 partial view, where an articular extension 2 shown in dashed outline of a prior art heart valve has intentionally been superposed on the articular extension 34 of the valve 10 of the invention.

On going from the old configuration of the articular extension 2 to the new configuration of the extension 34, the area of the articular extension 2 projected into the plane of FIG. 3 has been reduced by at least 50%.

As shown in FIGS. 1 to 4b, the articular extensions of the valve 10 of the invention have no opening passing through them, in contrast to the articular extensions of the prior art and in particular those disclosed in U.S. Pat. No. 6,395,024.

The fact that the articular extensions have no openings passing through them improves the behavior of the valve of the invention in relation to the flow when the valve is implanted in the aortic position.

In this position, the valve disclosed in U.S. Pat. No. 6,395,024 has six small openings symmetrically arranged two by two on each of the articular extensions the function of which is to clean the leading edge of the flaps when they are in their open (raised) position.

Given that in the aortic position the blood flow regime is one of high pressures, there occurs a phenomenon of shearing of the blood flow through the small opening. This leads to the creation of six lateral jets impinging at high speeds on the wall of the aorta and the result of this is to activate the coagulation phenomenon.

The direct consequence of this chain of events is the local formation of a bloodclot progressively limiting the movement of the flaps, thus risking eventual dysfunction of the valve and circulatory insufficiency that can lead to the death of the patient.

The absence of openings through the articular extensions avoids this risk.

The following description of the flap 18 shown in FIGS. 1, 4a, 4b, 5 and 7 applies identically to all the other flaps fitted to the valve 10 of the invention.

The flap 18 includes a central part 38 to opposite sides of which are symmetrically connected two lateral wings 40, 42 inclined to it (FIGS. 1 and 7).

The flap 18 is symmetrical with respect to a plane passing through the axis Z (the axis of symmetry) and perpendicular to the plane of FIG. 5.

The flap 18 has a leading edge 44 which, in the open position of the flap shown in FIGS. 1, 4a and 4b, is on the upstream side of the anterograde flow (arrow A) and, in the closed position, cooperates with specific means provided on the interior peripheral surface 16 of the annular support 12 (see below).

This leading edge 44 has a convex shape with a downwardly oriented curvature (see FIGS. 4a, 4b, 5 and 7) adapted to cooperate with the interior surface 16 of the valve.

The flap 18 also includes, on the side of the flap opposite the side on which the leading edge is situated, a trailing edge 46 that is on the downstream side of the anterograde flow.

As shown in FIGS. 1, 4a, 5 and 7, the trailing edge 46 comprises two symmetrical portions 46a and 46b that extend from the respective lateral wings 40 and 42 to a downstream end area 48 in which they join to form a point.

This point 48 is aligned along the axis of symmetry Z of the flap.

The portions 46a and 46b thus confer on the trailing edge 46 a substantially triangular inverted V-shape the tip of which coincides with the end area 48.

In the closed position of the valve (FIGS. 2 and 10), the trailing edges of the three flaps cooperate with each other to form a trihedron the tip whereof is directed downstream.

The end area 48 that can be seen in FIG. 7 showing the exterior surface 45 of the flap 18 is for example raised relative to the exterior surface of the flap to assume a shape that is substantially the shape of the tip of a ski.

It will be noted in this regard that this exterior surface has for example a plane general shape in a direction from one lateral wing of the flap to the opposite lateral wing.

More particularly, as shown in FIG. 9, the substantially ski tip shaped end 48 of the flap forms a tip that diverges from the extension of the interior surface 47 of the flap at an angle between substantially 2° and 4°.

Accordingly, when the flap is placed in the flow, the ski tip shaped end 48 of the flap is not parallel to the flow whereas the body of the flap is substantially parallel to the direction of the flow.

The presence of the raised free end 48 of each flap reinforces the hydrodynamic mechanism of anticipated closure of the flap accompanying the deceleration of the anterograde flow that is caused by the progressive establishment during this phase of a subtle positive pressure gradient between the external and internal surfaces of the flap.

FIG. 10 shows from above the flaps 18, 20, 22 of the valve 10 in their closed position, in which the ski tip shaped ends 48 are at least 50 microns apart. A central interstice 49 in the shape of a star with three branches is thus formed between the trailing edges of the flap.

This interstice prevents all risk of cavitation on closure of the flaps and prevents the generation of noise on closure by eliminating contact between the trailing edges of the flaps in their end areas 48.

Furthermore, if in the long term slight wear of the leading edge of the flaps appears at their surface of contact with the interior surface of the annular support, the flaps will be lowered significantly below the nominal closure angle but an interstice will nevertheless still be present to prevent contact between the end areas 48 of the trailing edges of the flaps.

It will be noted that each of the branches extends over a distance corresponding at least to one third of the total length of the trailing edge of the flaps.

As shown in FIGS. 1, 2, 4a, 4b, the flap 18, like all the other flaps, and in particular the flap 20 in FIGS. 1 to 3, cooperates with the interior peripheral surface 16 of the annular support 12 and, more specifically, with means for guiding rotation of the flap, as well as with bearing means that are arranged radially on the interior peripheral surface of the valve.

Articulated in this way to the internal peripheral surface 16, the flaps are able to rotate between their open position in FIG. 1 and their closed position in FIG. 2.

The means for guiding rotation of the flap comprise two profiled voids 50 and 52 within the thickness of the respective articular extensions 32 and 36 that form tracks or arcs for guiding and retaining the lateral wings of the flap. More particularly, these tracks or arcs cooperate with part of the trailing edge 46 of the flap situated in a so-called end portion of the lateral wings 40, 42 (FIGS. 3, 4a and 11).

The guiding arcs (FIG. 11) arranged symmetrically on the internal peripheral surface of each articular extension are described in more detail in French patent 2 642 960, to which reference may be made.

The valve 10 also includes a number of different bearing means for each flap on the interior peripheral surface 16 of the support 12.

In particular, two first lower bearing or supporting means 60, 62 for the flap 18 (FIGS. 4a and 4b) have a profiled hydrodynamic shape the cross section whereof increases in the flow direction of the anterograde flow. The profiled shape terminates at an upper end surface 60a, 62a of symmetrical arc shape the slope whereof is steeper on the side opposite the articular extensions, as FIG. 4b shows for the supporting means 62.

The upper end surface 62a cooperates with a contact area 44a of the leading edge 44 to establish surface contact between them on closure of the flap, when said contact area moves in the direction of the insertion base of the supporting means located on the internal peripheral surface 16 of the valve.

This surface contact distributes wear caused by the contact of the two members (the leading edge of the flap and the supporting means) over a surface instead of having contact along a line, as would be the case with the symmetrical profile of the supporting means 61 represented in dashed outline in FIG. 4b. The forces are therefore better distributed thanks to the asymmetrical profile of the head (upper end) of the supporting means 62 and, more particularly, thanks to the portion 62a1 of the head of the latter which has a radius of curvature sufficiently large to obtain surface contact with the rectilinear contact area 44a of the leading edge. The portion 62a1 has a substantially plane shape, for example, being produced in the form of a flat, thus conferring on the upper end surface 62a a convex profile on the side of the nearest articular extension and substantially a flat profile on the opposite side.

In its closed position the flap 18 rests with its leading edge 44 (FIG. 4a) on the upper end surfaces 60a, 62a of the supporting means, and, more particularly, on the flattened portions of those surfaces. In exactly the same way, two separate first lower supporting means of the same type as those described hereinabove are also provided on the valve for each of the other flaps: the bearing means 63, 65 for the flap 20 and the bearing means 67, 69 for the flap 22, as shown in FIG. 12.

The valve also includes second lower bearing or support means substantially in the middle and lower part of each articular extension (FIGS. 4a, 11 and 12) which take the form of a member 64, 66, 68 in the shape of a ship's prow pointing upward and profiled in the direction of the anterograde flow. Each of the profiled members 64, 66, 68 of the respective articular extensions 32, 36 and 34 has lateral edges sufficiently spaced (by a distance approximately equal to the thickness of the flaps) to serve as bearing points for the lateral edges of the flaps in their closed position.

Moreover, upper bearing means 70, 71 of the flap 18 (respectively 72, 74 and 76, 78 of the flaps 20 and 22) are provided on the downstream edge 30 of the annular support and offset axially along the longitudinal axis X relative to the first lower bearing means (see FIGS. 4a and 11).

Figure 12:
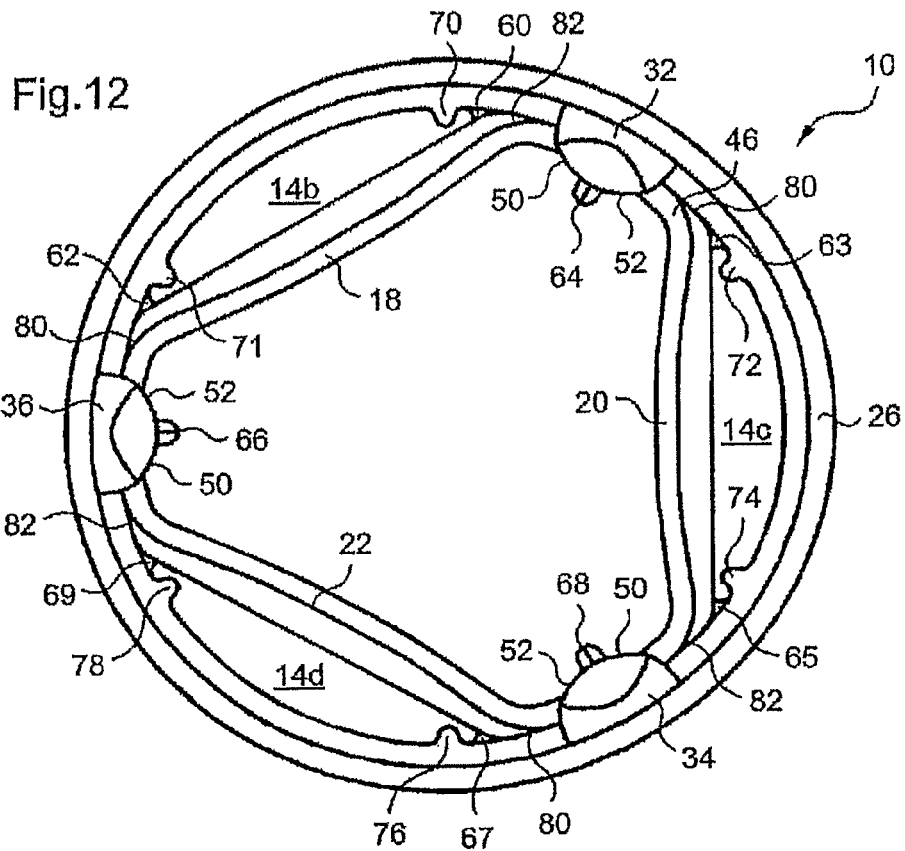
FIG. 12 is a diagrammatic top view of a valve of the invention with the flaps in their open position.

Moreover, as shown in FIGS. 11 and 12, the first lower bearing means 60 and 63 and the respective upper bearing means 70 and 72 of these flaps are offset radially relative to each other to prevent the upper bearing means from being placed in the wake of the first lower bearing means. This avoids the creation between these lower and upper bearing means of micro-disturbances of the flow that would encourage activation of the blood platelets.

This feature also ensures that the surfaces of the flap and the support situated between the first lower bearing means and the upper bearing means are swept sufficiently by the flow during the cardiac cycle. In particular, the upper end surface of each first lower support means is thoroughly exposed to the retrograde flow during closure of the valve.

The upper bearing means 70 and 71 of the flap 18 between the two articular extensions 32, 36 (FIG. 4*a*) with which the respective lateral wings of this flap cooperate serve as upper stops during opening movement of the flap. These stops thus cause the flap to pivot around its rotation axis, as described hereinafter, when the pressure of the flow of blood is exerted on the internal surface of this flap.

More particularly, the upper stops 70 and 71 come into contact with the upstream portion of the external surface of the flap during the first few milliseconds of opening of the valve.

When the blood pressure is exerted on the interior surface of the closed flap and raises it a few tenths of a millimeter (which is made possible by the play provided between the lower part of the stops and the upper exterior surface of the flap when the latter is resting on the end surfaces 60*a*, 62*a* of the first lower bearing means), the contact of the flap with these stops causes symmetrical pivoting of its two lateral wings about the rotation axis and raising of the flap. Because of this virtually instantaneous pivoting, the exterior surface of the flap moves away from the stops, thus forming between those stops and this surface of the flap a large passage for the blood flow.

It will moreover be noted that in their open position the flaps do not rest on the lower bearing means, which serve as supports only during the closure of the flaps.

Moreover, positioning the upper bearing means 70 and 71 between the first lower bearing means 60 and 62 significantly increases the volume of the upper bearing means, thus increasing the area of impact between the latter and the exterior surface of the flap in the vicinity of its leading edge. This reduces the concentration of mechanical stresses at the point of contact, which in the long term prevents possible deterioration of the local surface state of the flap.

It is nevertheless necessary not to have the upper bearing means too far away from the first lower bearing means in order to preserve the effect of synchronous and symmetrical opening of the two lateral wings of the flap and not to increase the volume of the upper bearing means in a proportion that could induce unnecessary disturbance of the blood flow.

For these reasons, in the embodiment described here, each upper bearing means 70, 71 is offset radially or angularly (in projection into a plane perpendicular to the axis X) from its nearest first lower bearing means 60, 62 by a distance that substantially corresponds to at least one times the radial dimension (width) of the first lower bearing means.

For example, for a heart valve with an outside diameter equal to 29 mm, the radial dimension or width of the lower bearing means is approximately 1.5 mm and the upper bearing means is therefore spaced radially by at least 1.5 mm from the wake of the corresponding first lower bearing means.

The upper bearing means (stop) are preferably wider in their upstream part and more tapered in their downstream part since only the upstream part comes into contact with the exterior surface of the flap when it opens and it is important to reduce locally the concentration of stresses on impact.

As represented in FIG. 4*a*, the leading edge 44 of the flap 18 is between the first lower bearing means 60, 62 and the upper bearing means 70, 71.

It will be noted that the rotation guide means of each flap define a rotation axis (represented in chain-dotted line in FIGS. 5 and 7) that extends in a direction from one lateral wing of the flap to the opposite lateral wing. The rotation axis is at a distance from the longitudinal axis X of the valve (in a plane perpendicular to that axis) that is greater than 75% of the radius of the annular support 12 of a flap whilst allowing blood to flow between the exterior surface of the flap and the interior peripheral surface 16 of the annular support.

Each rotation axis is virtual in that it is situated entirely outside the corresponding flap, between it and the annular support. The axis is therefore highly off-centered relative to the center of gravity of the flap. Thus the resultant of the friction forces on the flap imparts a movement relative to the virtual axis sufficient to initiate the closure of the flap on deceleration of the blood flow. This encourages the closure movement and makes it much less violent than with some prior art valves in which the flaps close sharply, causing both noise and trauma to the circulating blood cells.

This off-center disposition of the rotation axes of the flaps enables the flaps to be disposed, in the open position of the valve, substantially parallel to the axis of the blood flow, or even in a plane at significantly more than 90° to the plane perpendicular to the axis X, as the friction forces alone are sufficient to start their closure.

As already mentioned hereinabove, the presence of the raised extremity in the shape of a ski tip of the end area 48 of each flap contributes to encouraging precocious closing of the flaps by the natural forces of the flow upon deceleration of the flow.

Moreover, by moving the upper bearing means 70, 71 away from the first lower bearing means 60, 62 of the flap 18, the upper bearing means are moved away from the rotation axis of the flap and thus increase the required lever effect when the upper edge of the flap is raised because of the pressure exerted on its interior surface at the start of the phase of opening of the cardiac cycle.

A very weak hydrodynamic force supplied to the internal surface of the closed flap then causes virtually immediate symmetrical tilting of the flap about its rotation axis.

As already described hereinabove with reference to FIG. 4*a*, the articular extensions on the downstream edge of the annular support 12 are much smaller than the articular extensions of the prior art valves with three flaps.

Because of this, when the flaps are raised (valve in open position as in FIGS. 1, 3, 4*a*, 11 and 12) the exterior surface of each lateral wing of each of the flaps that bears against a lateral part of a corresponding articular extension is considerably smaller than in the prior art. As shown in FIGS. 3 and 11, only a fraction of the exterior surface of each lateral wing is in contact with a part of the articular extension whereas, in the prior art, virtually all of the exterior surface of each lateral wing of the flap 20 is against a much larger portion of the corresponding articular extension 2 (shown in dashed outline).

Accordingly, for the lateral wing 42 of the flap 20 in FIG. 3, only the exterior surface of the terminal portion 42*a*, called the articulation facet, of this lateral wing 42 faces and bears against a portion of the internal surface of the articular extension 34, called the extension facet.

In FIG. 11, there are represented in chain-dotted outline the articulation facets 42*a* and 40*a* of the lateral wings 42 and 40 of the respective flaps 18 and 20 in contact with the respective extension facets 50a and 52a of the articular extension 32.

It is thus seen that the fraction of the exterior surface of each lateral wing that would be masked by the articular extension 2 of the prior art valve is, thanks to the invention, no longer facing a material surface, which considerably reduces the risk of interposition of a biological deposit between this exterior surface fraction and the lateral internal surface of the articular extension. The notch provided in each articular extension thus enables a greater area of the lateral wings of each flap to be cleaned by the flow of blood during the cardiac cycle.

Eliminating non-biological surfaces in contact with each other in the flap pivoting space consequently eliminates, or at least reduces, the risk of coagulation biological deposition in this area.

Thus in practice the invention eliminates a critical risk of valve dysfunction leading to acute circulatory insufficiency.

It should be noted that the sum of the fractions of the exterior surfaces of the two lateral wings of each flap, i.e. of the articulation facets 40a and 42a, which in the open position of the flap are against the respective extension facets 52a and 50a of the corresponding articular extension, correspond to an area substantially less than 5% the total exterior area of the flap.

Theoretically, there is no lower limit for the areas of the two articulation facets, in that they should be as small as possible whilst effectively guiding rotation of the flap. However, in practice, a lower limit of 1% is achievable and the area of the two extension facets is thus equal to 1.4% of the total exterior area of the flap, for example.

It will be noted that to reduce the facing area of the two articulation facets the width of the base of each articular extension can be reduced relative to its width at its apex, with the result that the extension visible in FIG. 3 is more mushroom-shaped than crenellated.

The lateral flanks of the extension will thus be concave instead of substantially rectilinear as in FIG. 3.

By way of comparison, the sum of the fractions of the exterior areas of the lateral wings of a flap of the prior art valve described in U.S. Pat. No. 6,395,024 and that are in contact with part of the internal surface of two corresponding articular extensions is at least equal to 15% of the total exterior area of the flap.

Thus the improvement over the prior art provided by valves of the present invention and the impact that this can have on the preventive anticoagulation treatment to be used to prevent the risk of interposition of biological materials are clear.

It will be noted that this impact is greater for valves with three flaps because they comprise six pivoting spaces, compared to four for valves with two flaps.

FIGS. 6 and 8 show a flap 100 of a prior art mechanical prosthetic heart valve with three flaps, respective from above and in perspective.

In this figure, the flap 100 has two lateral wings 102 and 104 that are respectively connected to a central part 106 via junction areas 108, 110 each forming a convex area having a very low radius of curvature. Thus as far as the flow is concerned this connection area resembles an "edge" on the exterior surface of the flap.

The angle that each lateral wing forms with the central part of the flap is constant.

The Applicant has noticed that this "edge" on the exterior surface of the flap generates a singularity in the flow in the form of a small area of downstream recirculation in the immediate vicinity of the articulation and extension facets. This singularity increases the kinetic energy of the blood cells and in particular the platelets at this location, increases the time for which they remain on the surrounding surfaces, and consequently increases the risk of formation of coagulation deposits.

Eliminating as just explained in the description with reference to FIGS. 3, 4a, 11, and 12 a major portion of the lateral surface of the articular extensions that is adjacent this recirculation area reduces the risk of formation of biological coagulation deposits on the articulation and extension facets which define between them the pivoting spaces of the valve.

The phenomena referred to above of disturbance of the blood flow nevertheless persist because of the presence of the junction areas 108, 110 of each flap.

To prevent this, in the configuration of the valve of the invention, each of the lateral wings 40, 42 of each flap, for example the flap 18 represented in FIGS. 5 and 7, forms with the central part 38 to which it is connected a junction area 80, 82 with a convex exterior surface, the radius of curvature whereof is sufficiently large to prevent the formation of turbulent flow in the vicinity of this surface.

To be more specific, considering the length of this junction area that extends from the leading edge to the trailing edge (parallel to the axis Z), this radius of curvature must be sufficiently large over at least part of its length including the trailing edge 46 of the flap. Thus the radius of curvature in the vicinity of the leading edge 44 can have a low value and, over part of the length of this junction area that includes the trailing edge 46, a higher value that prevents the flow from separating from the exterior surface of the flap and generating local disturbances.

A low value of the radius of curvature in the vicinity of the leading edge enables the use of smaller lower supporting means, which therefore provide little obstruction to the flow.

However, the value of the radius of curvature increases in the direction of the anterograde flow along the flap, i.e. toward its trailing edge.

Figure 13:
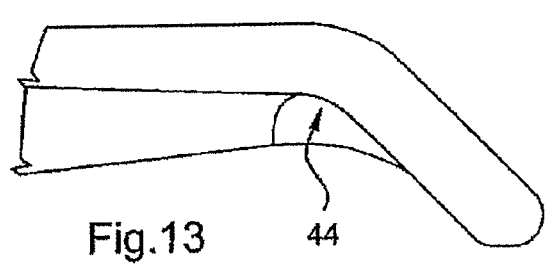
FIGS. 13 and 14 are diagrammatic partial views in the plane of the central part of a flap of the invention of the leading edge and the trailing edge of one of the junction areas of said flap, respectively.
Figure 14:
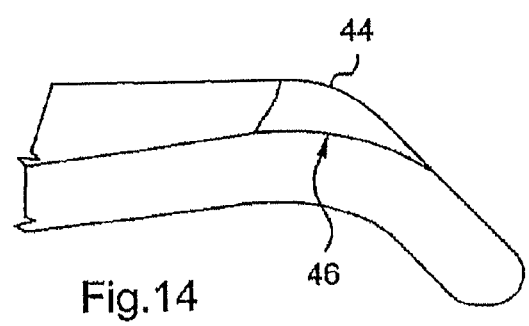

An embodiment conforming to this teaching is shown in FIGS. 5 and 7, for example, in which the convex exterior surface of the junction area 80, 82 adopts the general shape of a portion of a cone the apex whereof faces upstream in relation to the anterograde flow, i.e. from the side of the leading edge 44 of the flap, and the opening of the cone is at the trailing edge. It should be noted that the apex of the cone can be placed closer to or farther away from the leading edge according to the required shape. For example, the radius of curvature increases progressively from the leading edge, or the vicinity thereof, toward the trailing edge. FIGS. 13 and 14 are diagrammatic views in the plane of the flap of the leading edge 44 and the trailing edge 46, respectively.

It will be noted that the interior surface of the junction area 80, 82 also has the general shape of a portion of a cone.

The value of the radius of curvature at the leading edge for valves implanted in the aortic position is between 1 and 2 mm inclusive, for example equal to 1.15 mm for a valve having an outside diameter of 19 mm, and 1.5 mm for a valve having an outside diameter of 31 mm.

The radius of curvature at the trailing edge is at least 2 mm, more specifically between 2 and 4 mm inclusive, and is for example equal to 2.5 mm for a diameter of 19 mm and to 3.3 mm for a diameter of 31 mm.

The respective corresponding values of the radii of curvature on the interior surface of the flap are 0.5 and 0.6 mm for the leading edge and 1.5 and 1.8 mm for the trailing edge.

For valves implanted in the mitral position, the radius of curvature values at the leading edge are between 1 and 2 mm inclusive and, for example, equal to 1.32 mm for a valve with an outside diameter of 25 mm and to 1.5 mm for a valve with an outside diameter of 33 mm. They are at least 2 mm at the trailing edge, more specifically between 2 and 4 mm inclusive and, for example, equal to 2.9 mm for a diameter of 25 mm and to 3.3 mm for a diameter of 33 mm.

The respective corresponding values of the radii of curvature on the interior surface of the flap are 0.52 and 0.6 mm for the leading edge and 1.6 and 1.8 mm for the trailing edge.

It will be noted that if the radius of curvature between the central part and the lateral wing of the flap is increased at the leading edge, the extent of the area of contact between the upper end surface of the first lower supporting means and the leading edge of the flap, during the closure movement, increases significantly, which distributes wear even more. The initial area of contact at the start of closure is then shifted significantly toward the tip of the first supporting means rather than toward its insertion base.

However, a compromise must be achieved with regard to the radius of curvature at the leading edge in order for the lower supporting means to retain a reasonable size in relation to the flow.

For example, the angle at the apex of the cone (measured at the leading edge) is 50° plus or minus 5°.

To reduce further the hydrodynamic singularities generated in the flow by the flaps, the external surface 45 of the central part of the flap 18 has, for example, a substantially convex shape in a direction from the lateral wing 40 to the opposite lateral wing 42 (FIG. 15) instead of a plane general shape. This convex shape applies only to the area of the flap near the leading edge, between the rotation axis of the flap and the leading edge, the area of the flap downstream of the rotation axis being for its part somewhat concave. Thus the travel of the leading edge on the first lower supporting means is substantially shorter, thereby increasing the resistance to wear of the valve.

In another embodiment (not shown), the convex exterior surface of the junction area between the central part of the flap and each lateral wing adopts the general shape of part of a cylinder and the radius of curvature is therefore constant.

When such flaps are fitted to valves implanted in the aortic position, the radius of curvature on the exterior surface of the flaps is at least 2 mm, more specifically between 2 and 4 mm inclusive and, for example, equal to 2.5 mm for a valve with an outside diameter equal to 19 mm. It is between 2 and 4 mm inclusive and, for example, equal to 3.3 mm for a valve with an outside diameter equal to 33 mm for valves implanted in the mitral position.

The arrangement of the part-cylindrical junction area can be useful in some applications where the radius of curvature in the vicinity of the leading edge of the flap must not be made as small as possible.

It will be noted that, whatever the general shape of the junction area, to avoid the formation of turbulent flow in the vicinity of the articulation areas of the flaps (areas in which the lateral wings of the flaps cooperate with the articular extensions), the minimum radius of curvature at the trailing edge is 2 mm for valves intended to be implanted in the aortic position and 3 mm for valves intended for the mitral position.

Figure 16:
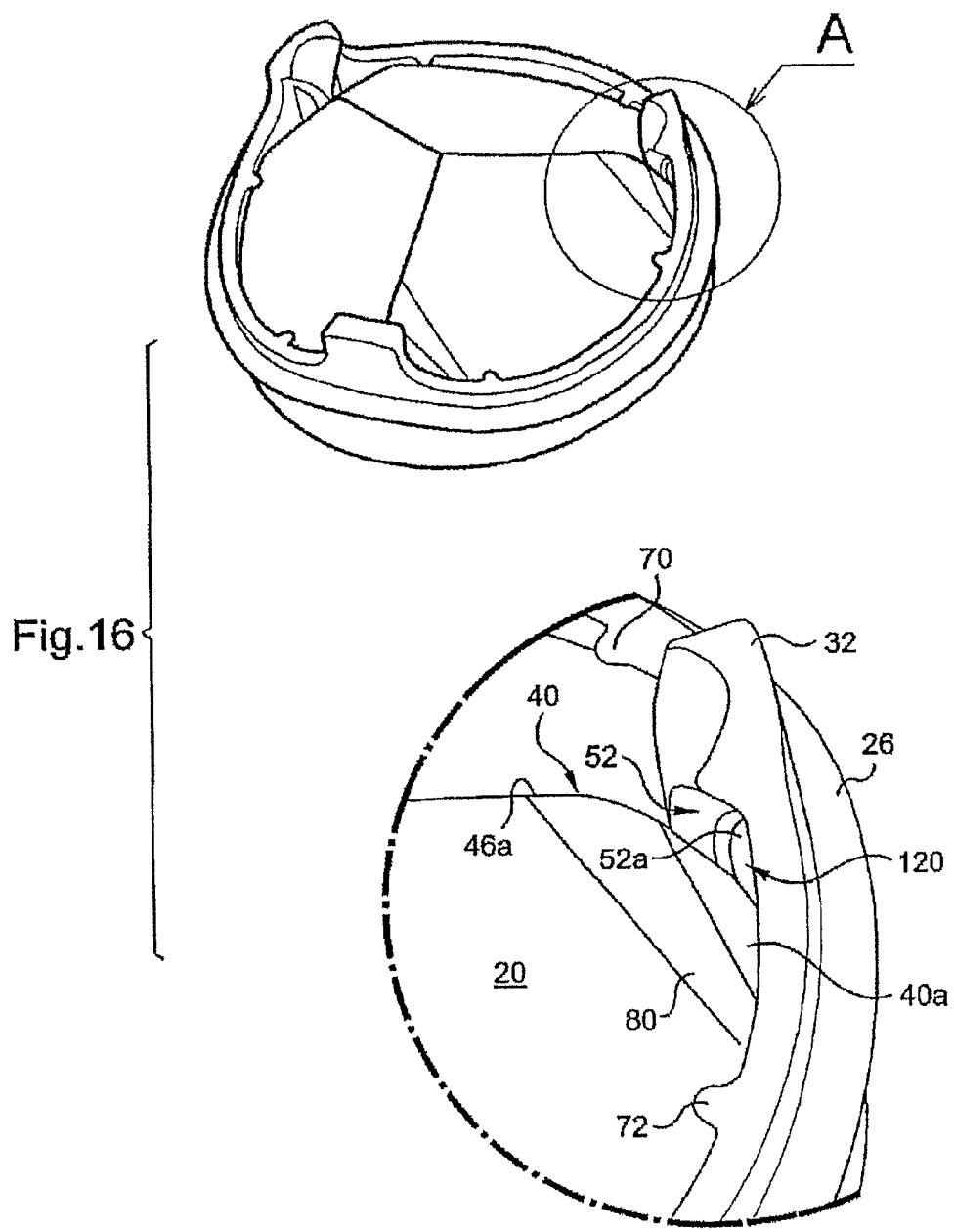
FIG. 16 is a diagrammatic partial view to a larger scale of a pivoting space of a valve of the invention.

When the flaps are in their closed position (FIGS. 2, 10, 16 and 17), each of the articulation facets of each flap (for example the facet 40a in FIG. 16) and the corresponding extension facet (for example the facet 52a in FIG. 16) of the articular extension concerned (extension 32 in FIG. 16) define between them a free space 120, referred to as the pivoting space of the flap, which has a three-dimensional geometrical shape that is difficult to represent figuratively.

This shape is defined theoretically by the volume developed by the movement in space of the articulation facet 40a of the flap during opening/closing movement of the flap.

When the flap is open (FIGS. 1, 3, 4a and 12), the articulation facet 40a is in contact with the corresponding extension facet 52a and the pivoting space 120 has disappeared.

It will be noted that the volume of the pivoting space is less than $2/100^{th}$ of the total volume displaced by a flap when it moves from the closed position to the open position, which volume is much smaller than the volume of the pivoting space of a prior art flap having the articular extension 2 from FIG. 3.

The valve in its closed position (FIGS. 2, 10 and 15) thus includes six pivoting spaces 120.

When the junction areas 80, 82 of the flaps have the shape of a portion of a cone or a frustum of a cone, it is found that the downstream part of these areas (situated on the side of the trailing edge 46) is lowered relative to the part of these areas on the upstream side, i.e. on the side of the leading edge 44 (FIGS. 12 and 14).

Figure 17:
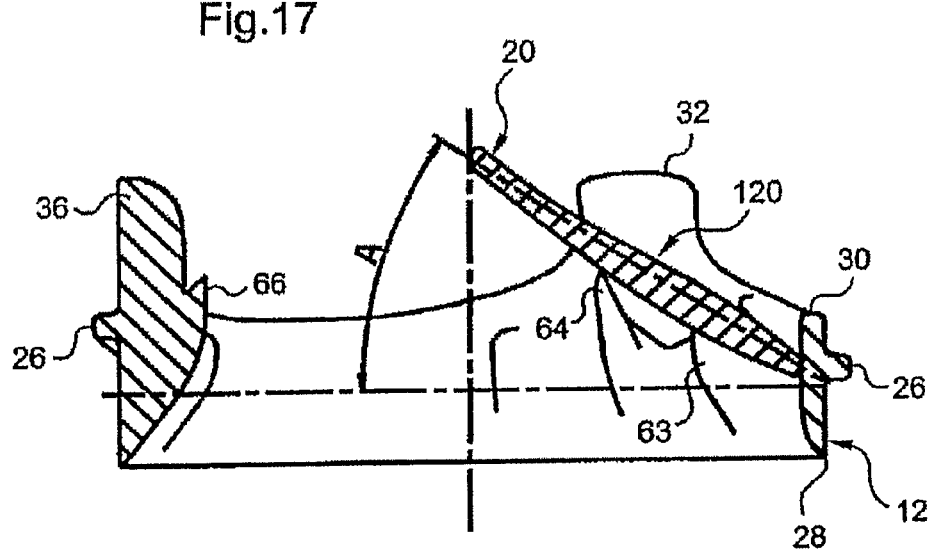
FIG. 17 is a diagrammatic partial view showing the inclination of a flap of a valve of the invention in its closed position.

Accordingly, in the closed position of the flaps, the area of association of the trailing edges of the flaps is, compared with the prior art, lowered relative to a plane perpendicular to the longitudinal axis X, such as the plane containing the leading edge 28 of the annular support 12 (FIG. 17).

The invention therefore reduces the angle A, known as the closure angle and represented in FIG. 17.

For valves intended to be implanted in the aortic position or in the mitral position, this angle is between 30° and 50° inclusive and an angle of 35° is particularly suitable for the aortic position. For valves intended to be implanted in the mitral position, an angle of up to 50° can prove advantageous. It will nevertheless be noted that a closure angle of 35° can be adopted for all sizes of aortic and mitral valves.

Moreover, because of the lowering of the trailing edges of the flaps relative to the horizontal in the closed position of the flap (FIG. 17), when the latter is bearing on the lower supporting means, the pivoting space 120 (FIG. 16) becomes more flared and more accessible to retrograde rinsing by the blood stream than in the prior art valves where this space is between less flared walls that represent a greater impediment to access for the flow.

Thus the invention reduces the risk of coagulation deposits forming and growing in this pivoting space.

It should be noted that the pivoting spaces of the valve with three rigid flaps are critical to the resistance of the valve to coagulation phenomena. The specific arrangement of this space in accordance with the invention has the aim of minimizing stasis on the adjacent walls (flaps and articular extensions), any singularity in the microstructure of the flow at this location and any foreign surface of no utility in its immediate vicinity.

Figure 15:
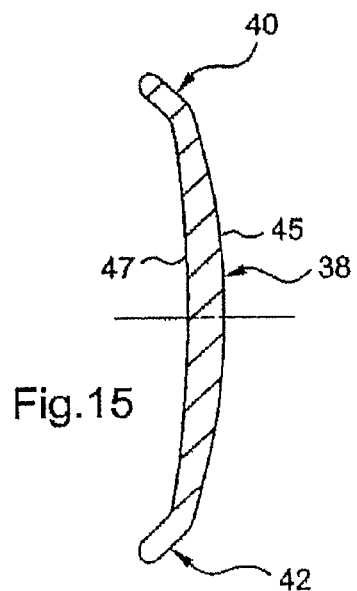
FIG. 15 is a diagrammatic view in section of a longitudinal section of a flap of the invention.

As represented more particularly in FIG. 15 and already explained above, the exterior surface 45 of the central part 38 of each flap is of substantially convex shape, for example, which increases the central area of the flaps exposed to the anterograde flow when the valve is in its open position. In conjunction with the arrangement of the junction area with an increased radius of curvature between the central part and the lateral wings of the flaps, the aim of this convexity is to distribute the flow uniformly over all of the exterior surface of the flaps and in particular over the lateral facets dedicated to pivoting. This is in contrast to the effect of the prior art disclosed in U.S. Pat. No. 6,395,024 in which the shape of the exterior surface of the flap tends to direct the flow away from the lateral wings in directing it toward the center of the flap along a path of lower resistance.

Accordingly, this configuration reduces the risks of biological interposition if implantation is not exactly orthogonal to the axis of the flow, which is not a rare occurrence in practice because of the local pathological modifications that surgeons often encounter when implanting a valve prosthesis.

In FIG. 12, showing the valve of the invention in its open position, it is seen that the internal passage 14 offered to the flow is divided into a main orifice 14*a* and three secondary orifices 14*b*, 14*c* and 14*d*.

The main orifice is delimited by the interior surfaces of the flaps.

The interior surface 47 of the central part of the flaps has, preferably in its upstream part, a concave general shape in a direction from one lateral wing 40 to the opposite lateral wing 42 (FIG. 15), which positions the upstream part of each flap including the leading edge in an area of anterograde blood flow in which the speeds are substantially slower than toward the center of the valve.

The upstream part is that situated between the leading edge and the rotation axis of the flap.

Thus the anterograde flow encountering the leading edge of the flaps is less subject to disturbances than with flaps the interior surface whereof is of convex shape in the plane of FIG. 15.

It will be noted that the main orifice is thus substantially widened compared to the prior art and the flow section offered to the flow by this orifice in a plane perpendicular to the axis X, notably in the part of the orifice defined by the upstream part of the flaps, is at least equal to 75% of the internal surface delimited by the support 12.

Each secondary orifice 14*b*, 14*c*, 14*d* is, for its part, defined by the space offered to the flow between the exterior surface of one of the three flaps and the internal peripheral surface portion of the support 12 that separates the articular extensions with which the flap concerned cooperates.

When the exterior surface of the flaps has a substantially convex general shape, the secondary orifices each have a crescent moon general shape.

These secondary orifices constitute orifices for rinsing the exterior surface of the flaps and in particular their lateral wings.

It will be noted that the largest flow section offered to the flow by each secondary orifice 14*b*-*d* in a plane perpendicular to the axis X is less than 7% of the internal surface delimited by the support 12.

Moreover, the dimension of each secondary orifice in a radial direction passing through the center of the support 12 in a plane perpendicular to the axis X is less than 20% of the inside radius of the support.

Figure 18:
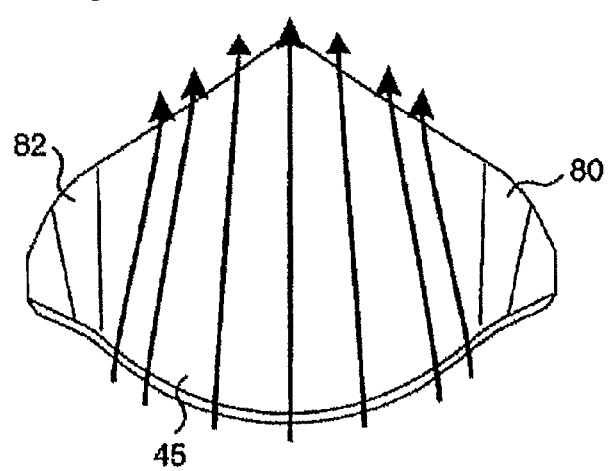
FIG. 18 is a diagrammatic representation of the flow of blood over the exterior surface of a flap of the invention with no grooves.

FIG. 18 shows the structure of the flow over the plane, or even concave, exterior surface 45 of a flap in its open position.

This is also the case if the exterior surface of the flap has the shape shown in FIG. 15 in the vicinity of the leading edge and then a somewhat concave shape in the downstream direction.

It is found that, generally speaking, the flow converges toward the central part of the flap, which encourages the cleaning of this part to the detriment of the lateral wings.

Figure 19:
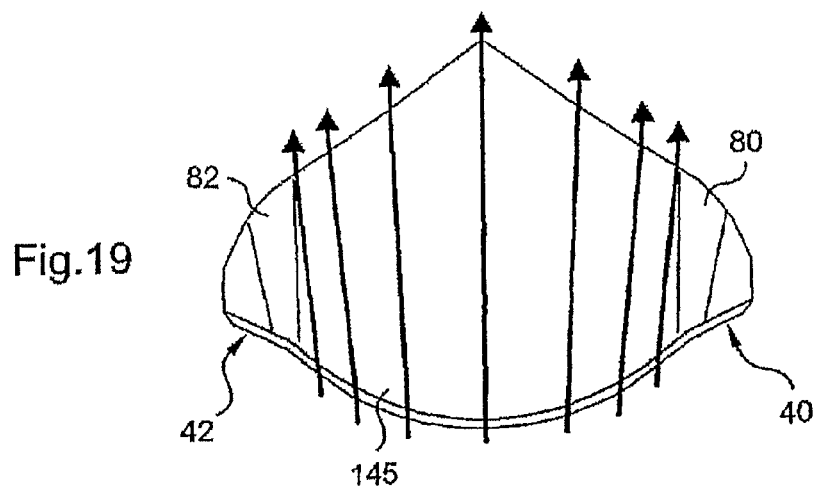
FIG. 19 is a diagrammatic view representing the flow of blood over the exterior surface of a flap of the invention with grooves.

To the extent that, as previously mentioned, the parts of the valve situated near the pivoting spaces thereof constitute critical areas that must be particularly well cleaned by the flow, the Applicant has modified the structure of the exterior surface of the flaps to encourage orientation of the blood flow toward the lateral wings of the flaps as shown in FIG. 19.

Figure 20:
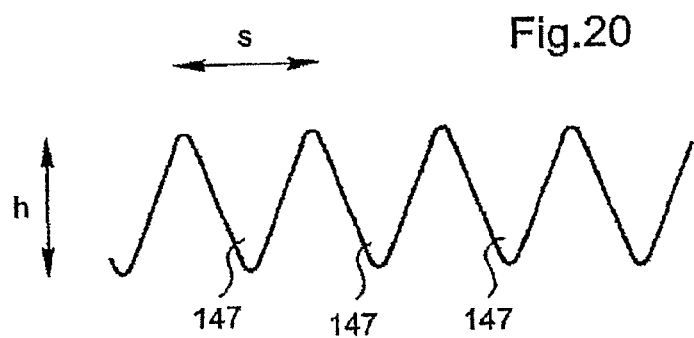
FIG. 20 is a diagrammatic partial view of one possible shape of grooves conforming to the invention.

The modified exterior surface 145 is thus provided with a plurality of grooves 147 represented by way of example in FIG. 20 with a V-shaped cross section and oriented so as to channel the blood flow in a controlled manner.

The grooves can be oriented differently according to the areas of the exterior surface of the flap in which they are formed: the grooves formed near the center of the flap are oriented axially along the axis Z of symmetry of the flap, while the grooves provided in the vicinity of the lateral wings 40, 42 have an axial orientation that forms with the axis Z an angle between 5° and 7° inclusive, for example.

This angle can be more pronounced the closer the grooves are to the wings.

Such an arrangement distributes the flow over a larger surface of the flap and thus encourages cleaning of the lateral wings.

It will be noted that other possible shapes of the cross section of the grooves can be envisaged: rounded U-shapes, rectangular shapes, trapezoidal shapes, L-shape wings, etc.

These grooves have a height h that corresponds substantially to the thickness of the boundary layer of the blood flow over the flap and is of the order of 0.01 mm, for example. Generally speaking, the thickness of the boundary layer can be obtained from the dimensions of a flap by applying a scale factor of $1/(\text{Reynolds' number})^{1/2}$.

It will be noted that the spacing (groove width) s in FIG. 20 can be increased if necessary.

To reduce the risk of contamination of the grooves, a minimum spacing s of 5 mm is effective.

It will also be noted that the distance between two consecutive grooves is adjusted as a function of the risks of contamination of the grooves.

Moreover, the grooves produced over all or part of the exterior surface of the flaps contribute to thickening and stabilizing the boundary layer of the flow, thus reducing turbulent friction and friction drag resulting therefrom generated by the encounter of the flow and the exterior surface of the flaps.

These grooves are obtained in known manner, for example, by molding if the flaps are produced in biocompatible polymers or by depositing isotropic diamond a few microns thick if the flaps are manufactured from another material or by micromachining.

It should be noted that the interior surface of the flaps can also be grooved to encourage a different distribution of the flow.

The peripheral rib 26 provided for fixing a ring of suture (not shown) is specifically configured, for example, so that its general shape, seen in FIGS. 1 to 3, reproduces the profile of a substantially sinusoidal curve.

Accordingly, the summits of the sinusoidal curve (the curvature of these summits has been intentionally exaggerated to make them more visible) are respectively arranged in line with each of the articular extensions 32, 34, 36 (summit 26*a* in line with the extension 34) of the support and the hollows are respectively arranged between two consecutive articular extensions: the hollow 26*b* is arranged between the extensions 34 and 36, while the hollow 26*c* is arranged between the extensions 32 and 34.

To some extent, it may be said that the profile of the rib 26 generally follows the contour of the trailing edge 30 of the support 12.

Different materials can be used to fabricate the valve of the invention with rigid flaps.

A biocompatible metal such as titanium or stellite is chosen for the annular support, for example.

Solid carbon can equally be used, or even a coating of carbon on graphite.

The flaps can for their part be produced from a biocompatible material, for example monolithic carbon, or in graphite with a pyrolytic carbon coating.

The flaps can also be produced in a biocompatible synthetic polymer that has properties of resistance to wear comparable to those pyrolytic carbon.

Thus a material such as PEEK (polyether ether ketone) has a low specific gravity of the order of 1.2 and is particularly suitable for fabricating the flaps.

This material is reinforced with carbon in order to increase the resistance to wear of the flaps.

One such material is supplied by the company Ensinger GmbH & Co., D-93413 Germany, for example. A material of this kind suitable for medical use is also available from the British company Invibio Ltd.

It will be noted that the valve of the invention can be produced in titanium for the annular support 12 and in PEEK for the flaps, this pair of materials being perfectly suitable for the friction and wear encountered in this type of valve.

Moreover, PEEK can equally be used as the material for fabricating the flaps with pyrolytic carbon used for the support, or pyrolytic carbon can even be used for the flaps and the support.

Such a choice of materials can furthermore be adopted for other types of heart valve with rigid flaps, independent of the invention.

The invention claimed is:

1. A mechanical prosthetic heart valve, comprising:
an annular support having an internal peripheral surface delimiting an interior that is centered on a longitudinal axis; and
at least two mobile flaps articulated to the internal peripheral surface of the support so that each of the flaps is able to rotate about a flap rotation axis perpendicular to the longitudinal axis from an open position of the valve, in which the flaps in the open position delimit between them a main orifice centered on the longitudinal axis and through which blood flows axially, to a closed position of the valve, in which the flaps in the closed position prevent the blood from flowing back through the main orifice,
the annular support having a downstream edge on a downstream side of an anterograde flow, and a plurality of articular extensions formed by respective portions of the downstream edge that each protrude axially in the downstream direction from respective opposing concave portions of the downstream edge, each articular extension having two opposite-facing sides running along the longitudinal axis in the downstream direction and terminating at an apex,
said two opposite-facing sides comprising curved-portions of the downstream edge that curve along opposite-facing concave paths, said apex formed by a length of the downstream edge connecting the two sides, and the respective curved portions of the two sides each comprise at least a point for which a correspondent tangent line is substantially parallel to the longitudinal axis, a quantity of said plurality of articular extensions corresponding to a quantity of flaps,
said articular extensions accommodating articulation areas with which the flaps cooperate to pass from the open position to the closed position and vice-versa,
each of the flaps having a central part symmetrically bracketed by two lateral wings that are inclined relative to said central part,
said central part having an exterior-facing surface,
the central part of each flap also having an interior surface facing toward the main orifice,
said two lateral wings respectively cooperating, to allow rotation of the flap, with internal surfaces of two articular extensions via a terminal portion of each lateral wing, each terminal portion having an exterior surface portion that defines an articulation facet that, when the flap is open, comes to bear against a corresponding articular extension facet formed by a portion of the internal surface of a corresponding articular extension, an area of the two articulation facets of each flap that contacts a corresponding articular extension facet together adding up to an area less than 5% of a total exterior area of the flap.

2. The valve according to claim 1, wherein each lateral wing of each of the flaps is connected to the central part of the flap by a junction area, an exterior surface of each junction area being convex and having a conical shape, an apex of said conical shape being located at an upstream side of the anterograde flow.

3. The valve according to claim 1, wherein each lateral wing of each of the flaps is joined to the central part of the flap by a junction area, an exterior surface of said junction area being convex and having a semi-cylindrical shape.

4. The valve according to claim 1, wherein the rotation axis of each flap is a virtual axis situated externally of the flap, between the flap and the annular support, and extends in a direction from the one lateral wing of the flap to the opposite lateral wing.

5. The valve according to claim 4, wherein the annular support has a given radius, and in that, in a plane perpendicular to the longitudinal axis of the valve, the flap rotation axis being at a distance from the longitudinal axis that is greater than 75% of the radius of the annular support.

6. The valve according to claim 1, wherein each of the articulation facets of a flap and the corresponding extension facet of the articular extension concerned define between them, when the flap is in the closed position, a flap pivoting space that disappears when the articulation facet of the flap comes, in the open position, to bear against the corresponding extension facet.

7. The valve according to claim 6, wherein the volume of the flap pivoting space is less than $2/100^{th}$ of the volume displaced by the flap when the flap moves from the closed position to the open position.

8. The valve according to claim 1, wherein the exterior surface of the central part of the flap has a convex shape in a direction from the one lateral wing to the opposite lateral wing.

9. The valve according to claim 1, wherein, when the valve is in the open position, a main orifice is delimited by the interior surfaces of the flaps and an internal area delimited in the same plane by the annular support, the main orifice having, projected in a plane perpendicular to the longitudinal axis of the annular support, a flow section offered to the flow that is equal at least to 75% of the internal area.

10. The valve according to claim 1, wherein, when the valve is in the open position, each flap defines a secondary orifice between an exterior surface thereof and an internal peripheral surface portion of the annular support that separates the two articular extensions with which the flap cooperates.

11. The valve according to claim 10, wherein each secondary orifice has a crescent moon shape.

12. The valve according to claim 10, wherein a dimension of the secondary orifice in a radial direction projected in a plane perpendicular to the longitudinal axis of the annular support is less than 20% of an inside radius of the annular support.

13. The valve according to claim 10, wherein each secondary orifice has in a plane perpendicular to the longitudinal axis of the annular support a flow section offered to the flow that is less than 7% of the internal area delimited in the same plane by the annular support.

14. The valve according to claim 1, wherein each of the articular extensions is free of any opening through a thickness thereof.

15. The valve according to claim 1, wherein the annular support has for each flap on an internal peripheral surface thereof, in a vicinity of the downstream edge, two stops that cause the flap to pivot into the open position when a pressure of the flow of blood is exerted on an internal face of the flap.

16. The valve according to claim 15, wherein for each flap, the annular support has on the internal peripheral surface thereof two supporting means for supporting the flap in the closed position, said supporting means for each flap being between the two articular extensions with which the respective lateral wings of the flap cooperate.

17. The valve according to claim 16, wherein, projected in a plane perpendicular to the longitudinal axis of the annular support, each stop is spaced angularly from a nearest supporting means by a distance corresponding to at least half a width of said supporting means, the width being measured in the plane concerned in a tangential direction relative to the annular support.

18. The valve according to claim 17, wherein the stops for each flap are between the supporting means of the flap.

19. The valve according to claim 16, wherein each flap has, at a periphery thereof, a leading edge that is on an upstream side of the anterograde flow of blood and cooperates with the internal surface of the annular support in the closed position of the flap and a trailing edge on the downstream side of the anterograde flow.

20. The valve according to claim 19, wherein each of the flap supporting means cooperates with a contact area of the leading edge of the flap through surface contact on closure of said valve.

21. The valve according to claim 20, wherein each flap supporting means has an upper end forming a head having a convex profile, a portion of a surface of the head on a side opposite the nearest articular extension being sloped and having a curvature that cooperates, with surface contact, with a transverse rectilinear contact area of the leading edge of the flap.

22. The valve according to claim 19, wherein the trailing edge of each flap has a triangular shape, and in the closed position of the valve, the trailing edges of the three flaps cooperate with each other to form a trihedron the apex of which is directed downstream.

23. The valve according to claim 1, wherein each flap in the closed position forms, with a plane perpendicular to the longitudinal axis of the annular support, a closure angle between 30° and 50° inclusive, and
wherein each flap, in an open position, is parallel to the direction of the flow.

24. The valve according to claim 1,
wherein the valve comprises three of the mobile flaps, and each of the flaps has, in the central part of the flap, at a trailing edge of the flap, an end area aligned with an axis of symmetry of the flap that is ski-tip shaped forming a tip that diverges from the extension of the interior surface of said flap, and
wherein, in a fully closed position of the valve in which the lateral wings of the flaps are contacting each other, said ski-tip shaped end areas of the flaps remain at a distance from each other forming therebetween a central interstice having a star shape.

25. The valve according to claim 24, wherein the ski-tip shaped end area diverges from the extension of the interior surface of the flap at an angle between 2° to 4° inclusive.

26. The valve according to claim 24, wherein, in the fully closed position of the valve, the three ski-tip shaped end areas remain at a distance from each other of at least 50 microns.

27. The valve according to claim 24, wherein each one of the respective ski-tip shaped end areas forms a tip that diverges from the extension of the interior surface of the flap, each of said tips extending over a distance corresponding at least to one-third of a total length of the trailing edge of the flap.

28. The valve according to claim 1,
wherein the valve comprises three of the mobile flaps, and each of the flaps has, in the central part of the flap, at a trailing edge of the flap, an end area aligned with an axis of symmetry of the flap that is ski-tip shaped forming a tip that diverges from the extension of the interior surface of said flap, and
wherein the ski-tip shaped end area of each one of the flaps forms a tip that diverges from the extension of the interior surface of the flap so that, in a fully closed position of the valve in which the lateral wings of the flaps are contacting each other, said ski-tip shaped end areas of the flaps remain at a distance from each other forming therebetween a central interstice having a star shape.

29. The valve according to claim 1,
wherein for each flap, the annular support has on the internal peripheral surface thereof two supporting means that support the flap in the closed position, said supporting means for each flap being located between the two articular extensions with which the respective lateral wings of the flap cooperate,
wherein each supporting means has an upper end forming a head having a convex profile, a portion of a surface of the head on a side opposite the nearest articular extension being sloped and having a curvature that cooperates, with surface contact, with a transverse rectilinear contact area of the leading edge of the flap.

30. The valve according to claim 29,
wherein the annular support has for each flap on an internal peripheral surface thereof, two upper bearing stops that cause the flap to pivot into the open position when a pressure of the flow of blood is exerted on an internal face of the flap, the upper bearing stops being offset radially with respect to a circumference of the annular support relative to the lower bearing means and offset axially with respect to the annular support along the longitudinal axis relative to the lower bearing means.

31. The valve according to claim 30,
wherein each upper bearing stop is offset radially with respect to a circumference of the annular support from its nearest lower bearing means by a distance of at least one times a radial width of the nearest lower bearing means.

32. The valve according to claim 1, wherein a base of each articular extension from which said articular extension protrudes in the downstream direction has a width that is substantially same as a width at the apex.

33. The valve according to claim 1, wherein the area of the two articulation facets of each flap that contacts the corresponding articular extension facet together adds up to an area of 1.4% of the total exterior area of the flap.

34. A mechanical prosthetic heart valve, comprising:
an annular support having an internal peripheral surface delimiting an interior that is centered on a longitudinal axis; and
at least two mobile flaps articulated to the internal peripheral surface of the support so that each of the flaps is able to rotate about a flap rotation axis perpendicular to the longitudinal axis from an open position of the valve, in which the flaps in the open position delimit between them a main orifice centered on the longitudinal axis and through which blood flows axially, to a closed position of the valve, in which the flaps in the closed position prevent the blood from flowing back through the main orifice,
the annular support having a downstream edge on a downstream side of an anterograde flow, and a plurality of articular extensions formed by respective portions of the downstream edge that each protrude axially in the downstream direction from respective opposing concave portions of the downstream edge, each articular extension having two opposite-facing sides running along the longitudinal axis in the downstream direction and terminating at an apex,
said two opposite-facing sides comprising curved-portions of the downstream edge that curve along opposite-facing concave paths, said apex formed by a length of the downstream edge connecting the two sides, and a base of each articular extension having a width that is equal to a width at the apex, a quantity of said plurality of articular extensions corresponding to a quantity of flaps,
said articular extensions accommodating articulation areas with which the flaps cooperate to pass from the open position to the closed position and vice-versa,
each of the flaps having a central part symmetrically bracketed by two lateral wings that are inclined relative to said central part,
said central part having an exterior-facing surface,
the central part of each flap also having an interior surface facing toward the main orifice,
said two lateral wings respectively cooperating, to allow rotation of the flap, with internal surfaces of two articular extensions via a terminal portion of each lateral wing, each terminal portion having an exterior surface portion that defines an articulation facet that, when the flap is open, comes to bear against a corresponding articular extension facet formed by a portion of the internal surface of a corresponding articular extension, an area of the two articulation facets of each flap that contacts a corresponding articular extension facet together adding up to an area less than 5% of a total exterior area of the flap.

* * * * *